United States Patent
Swerdloff

(10) Patent No.: US 10,946,220 B2
(45) Date of Patent: Mar. 16, 2021

(54) METHOD OF PROVIDING ROTATIONAL RADIATION THERAPY USING PARTICLES

(71) Applicant: Elekta, Inc., Atlanta, GA (US)

(72) Inventor: Stuart Julian Swerdloff, Dunedin (NZ)

(73) Assignee: Elekta, Inc., Atlanta, GA (US)

( * ) Notice: Subject to any disclaimer, the term of this patent is extended or adjusted under 35 U.S.C. 154(b) by 0 days.

(21) Appl. No.: 16/290,372

(22) Filed: Mar. 1, 2019

(65) Prior Publication Data

US 2020/0276456 A1  Sep. 3, 2020

(51) Int. Cl.
*A61N 5/10* (2006.01)

(52) U.S. Cl.
CPC .......... *A61N 5/1081* (2013.01); *A61N 5/103* (2013.01); *A61N 5/1049* (2013.01); *A61N 5/1067* (2013.01); *A61N 5/1071* (2013.01); *A61N 2005/1052* (2013.01); *A61N 2005/1061* (2013.01); *A61N 2005/1087* (2013.01)

(58) Field of Classification Search
CPC .... A61N 5/1081; A61N 5/103; A61N 5/1049; A61N 5/1067; A61N 2005/1052; A61N 2005/1071; A61N 2005/1061; A61N 2005/1087; A61N 5/1082; A61N 5/1043; A61N 5/1077; A61N 5/1071
See application file for complete search history.

(56) References Cited

U.S. PATENT DOCUMENTS

| | | | | |
|---|---|---|---|---|
| 5,427,097 | A | * | 6/1995 | Depp ................ A61N 5/1049 600/427 |
| 5,818,902 | A | * | 10/1998 | Yu ..................... A61N 5/1047 378/65 |
| 7,834,336 | B2 | | 11/2010 | Boeh et al. |
| 8,536,547 | B2 | | 9/2013 | Maurer, Jr. et al. |
| 8,658,992 | B2 | * | 2/2014 | Otto .................. A61N 5/1047 250/492.1 |
| 8,670,523 | B2 | | 3/2014 | Yan et al. |

(Continued)

FOREIGN PATENT DOCUMENTS

EP          3549636       10/2019
JP         2007525249      9/2007

(Continued)

OTHER PUBLICATIONS

Battinelli, Cecilia, "Proton Arc Therapy Optimization", Royal Institute of Technology School of Engineering Sciences, (2019), 94 pgs.

(Continued)

*Primary Examiner* — Wyatt A Stoffa
(74) *Attorney, Agent, or Firm* — Schwegman Lundberg & Woessner, P.A.; Sanjay Agrawal

(57) ABSTRACT

Techniques are described herein for delivering a particle beam composed of a plurality of beamlets from a continuously rotating gantry towards a target, by determining a plurality of predefined spots on the target and configuring them into a set of smaller spots on the outside of the target and a set of larger spots on the inside of the target, optimizing the delivery of the rotating particle beam such that the inside edge and the outside edge of the arc of the rotating beam are delivered to the spots located at the center of the target, and the central component of the arc of the beam is delivered to the spots located at the outside of the target.

34 Claims, 20 Drawing Sheets

CLOCKWISE SPIRAL

(56) References Cited

U.S. PATENT DOCUMENTS

| | | | |
|---|---|---|---|
| 9,561,389 B2* | 2/2017 | Luan | A61N 5/10 |
| RE47,173 E * | 12/2018 | Stokes | A61N 5/1042 |
| 10,166,408 B2 | 1/2019 | Michaud et al. | |
| 10,668,300 B2* | 6/2020 | Hissoiny | A61N 5/1039 |
| 2010/0176309 A1* | 7/2010 | Mackie | A61N 5/10 250/492.3 |
| 2011/0163245 A1* | 7/2011 | Stokes | A61N 5/1082 250/492.1 |
| 2012/0264998 A1* | 10/2012 | Fujitaka | A61N 5/1043 600/1 |
| 2015/0087887 A1* | 3/2015 | Iwata | A61N 5/1042 600/1 |
| 2016/0325119 A1* | 11/2016 | Yu | A61N 5/1047 |
| 2017/0056690 A1* | 3/2017 | Balakin | A61N 5/1068 |
| 2017/0273643 A1* | 9/2017 | Maurer, Jr. | A61N 5/1081 |
| 2018/0256919 A1* | 9/2018 | Shen | A61N 5/1043 |
| 2019/0091488 A1* | 3/2019 | Ding | A61N 5/1043 |
| 2019/0151683 A1* | 5/2019 | Roberts | A61N 5/1049 |

FOREIGN PATENT DOCUMENTS

| | | |
|---|---|---|
| WO | WO-2016116868 A1 | 7/2016 |
| WO | 2019154605 | 8/2019 |
| WO | 2019164835 | 8/2019 |
| WO | WO-2020180198 A1 | 9/2020 |

OTHER PUBLICATIONS

Cao, Wenhua, "Proton energy optimization and reduction for intensity-modulated proton therapy", Phys.Med. Biol. 59, (2014), 15 pgs.

Ding, Xuanfeng, "Have we reached proton beam therapy dosimetric limitations? -A novel robust, delivery-efficient and continuous spot-scanning proton arc (SPArc) therapy is to improve the dosimetric outcome in treating prostate cancer", Acta Oncologica, (Aug. 3, 2017), 4 pgs.

Freeman, Tami, "Proton arc therapy: the next evolution in proton delivery?", Physics World, (Oct. 16, 2019), 3 pgs.

Kabolizadeh, Peyman, "Defining the Future of Radiation Oncology: Latest Updates on Proton Arc Therapy", Beaumont, (Nov. 11, 2018), 14 pgs.

Kohno, Ryosuke, "Development of Continuous Line Scanning System Prototype for Proton Beam Therapy", International Journal of Particle Therapy, (2017), 10 pgs.

Kraus, Kim Melanie, "Dose Delivery Study for a Novel Compact Proton Accelerator", Dissertation, (Jan. 15, 2014), 143 pgs.

Yi, Byong Yong, "Proton Arc Therapy with Modulating Proton Energies", University of Maryland Ventures, (May 1, 2018), 3 pgs.

"International Application Serial No. PCT/NZ2020/050018, International Search Report dated May 4, 2020".

"International Application Serial No. PCT/NZ2020/050018, Written Opinion dated May 4, 2020", 7 pgs.

* cited by examiner

COUNTER-CLOCKWISE SPIRAL

CLOCKWISE SPIRAL

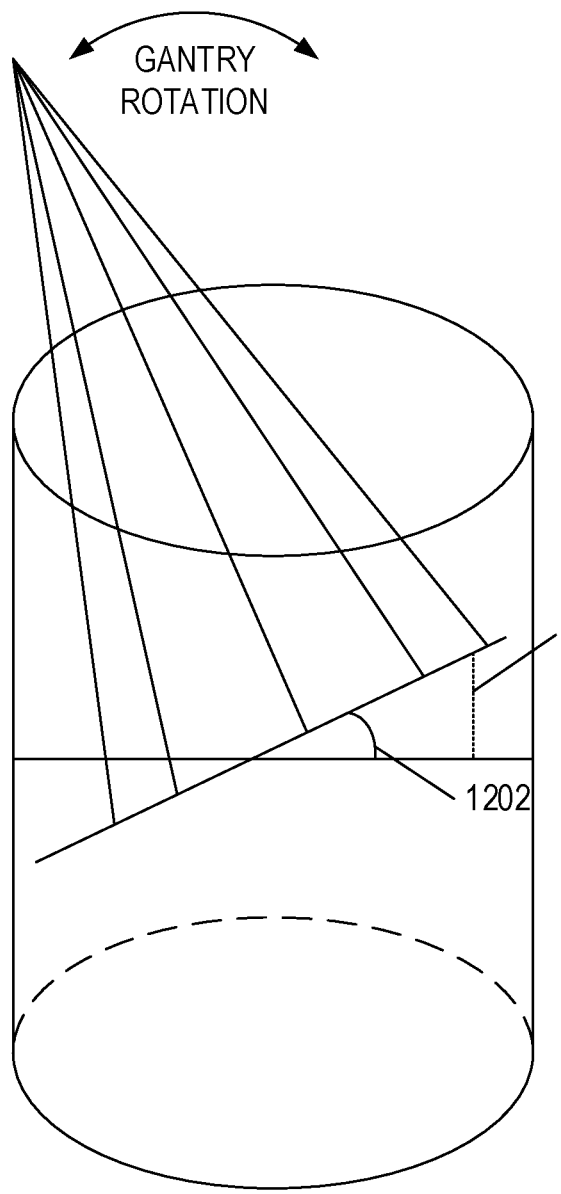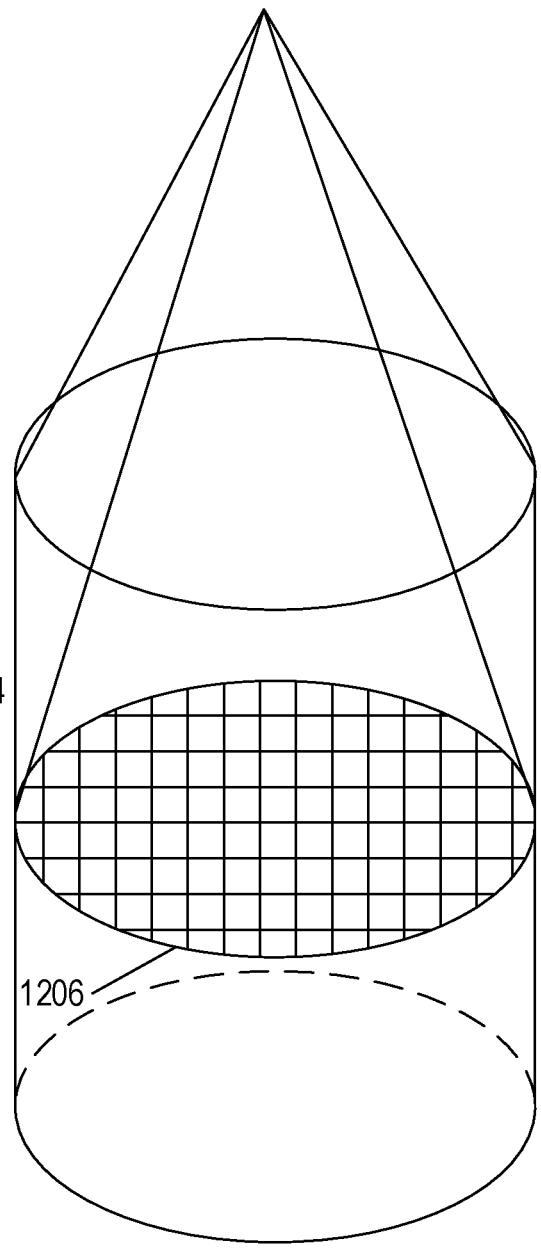
FIG. 12A                        FIG. 12B

0 DEGREE BEAM + 315 DEGREE BEAM + 90 DEGREE BEAM

METHOD OF PROVIDING ROTATIONAL RADIATION THERAPY USING PARTICLES

BACKGROUND

Radiation therapy or "radiotherapy" may be used to treat cancers or other ailments in mammalian (e.g., human and animal) tissue. One such radiotherapy technique is referred to as "gamma knife," by which a patient is irradiated using a number of lower-intensity gamma rays that converge with higher intensity and high precision at a targeted region (e.g., a tumor). In another example, radiotherapy is provided using a linear accelerator ("linac"), whereby a targeted region is irradiated by high-energy particles (e.g., electrons, high-energy photons, and the like). In another example, radiotherapy is provided using a heavy charged particle accelerator (e.g. protons, carbon ions, and the like), The placement and dose of the radiation beam is accurately controlled to provide a prescribed dose of radiation to the targeted region. The radiation beam is also generally controlled to reduce or minimize damage to surrounding healthy tissue, such as may be referred to as "organ(s) at risk" (OARs). Radiation may be referred to as "prescribed" because generally a physician orders a predefined dose of radiation to be delivered to a targeted region such as a tumor.

Generally, ionizing radiation in the form of a collimated beam is directed from an external radiation source toward a patient. Modulation of a radiation beam may be provided by one or more attenuators or collimators (e.g., a multi-leaf collimator). The intensity and shape of the radiation beam may be adjusted by collimation avoid damaging healthy tissue (e.g., OARs) adjacent to the targeted tissue by conforming the projected beam to a profile of the targeted tissue.

The treatment planning procedure may include using a three-dimensional image of the patient to identify the target region (e.g., the tumor) and such as to identify critical organs near the tumor. Creation of a treatment plan may be a time consuming process where a planner tries to comply with various treatment objectives or constraints (e.g., dose volume histogram (DVH) objectives or other constraints), such as taking into account importance (e.g., weighting) of respective constraints in order to produce a treatment plan that is clinically acceptable. This task may be a time-consuming trial-and-error process that is complicated by the various organs at risk (OARs) because as the number of OARs increases (e.g., about thirteen for a head-and-neck treatment), so does the complexity of the process. OARs distant from a tumor may be more easily spared from radiation, but OARs close to or overlapping a target tumor may be more difficult to spare from radiation exposure during treatment.

Generally, for each patient, an initial treatment plan may be generated in an "offline" manner. The treatment plan may be developed well before radiation therapy is delivered, such as using one or more medical imaging techniques. Imaging information may include, for example, images from X-rays, Computed Tomography (CT), nuclear magnetic resonance (MR), positron emission tomography (PET), single-photon emission computed tomography (SPECT), or ultrasound. A health care provider, such as a physician, may use three-dimensional imaging information indicative of the patient anatomy to identify one or more target tumors along with the organs at risk near the tumor. The health care provider may delineate the target tumor that is to receive a prescribed radiation dose using a manual technique, and the health care provider may similarly delineate nearby tissue, such as organs, at risk of damage from the radiation treatment.

Alternatively or additionally, an automated tool (e.g., ABAS® provided by Elekta AB, Sweden) may be used to assist in identifying or delineating the target tumor and organs at risk. A radiation therapy treatment plan ("treatment plan") may then be created using an optimization technique based on clinical and dosimetric objectives and constraints (e.g., the maximum, minimum, and mean doses of radiation to the tumor and critical organs).

The treatment planning procedure may include using a three-dimensional image of the patient to identify the target region (e.g., the tumor) and to identify critical organs near the tumor. Image acquisition may be performed just before initiation of delivery of a specified radiation therapy fraction. Such imaging may provide information helpful for identifying a position of a target region or for identifying motion of the target region. Such contemporaneous imaging may be referred to generically as "real-time," but in general a latency or time delay exists between an acquisition of an image and a delivery of radiation therapy.

Creation of a treatment plan may be a time consuming process where a planner tries to comply with various treatment objectives or constraints (e.g., dose volume histogram (DVH) objectives), taking into account their individual importance (e.g., weighting) in order to produce a treatment plan that is clinically acceptable. This task may be a time-consuming trial-and-error process that is complicated by the various organs at risk (OARs) because as the number of OARs increases (e.g., up to thirteen for a head-and-neck treatment), so does the complexity of the process. OARs distant from a tumor may be easily spared from radiation, while OARs close to or overlapping a target tumor may be difficult to spare.

The treatment plan may then be later executed by positioning the patient and delivering the prescribed radiation therapy. The radiation therapy treatment plan may include dose "fractioning," whereby a sequence of radiation therapy deliveries are provided over a predetermined period of time (e.g., 45 fractions or some other total count of fractions), such as with each therapy delivery including a specified fraction of a total prescribed dose. During treatment, the position of the patient or the position of the target region in relation to the treatment beam is important because such positioning in part determines whether the target region or healthy tissue is irradiated.

In one approach, radiation therapy may be provided by using particles, such as protons, instead of electrons. This typically may be referred to as proton therapy. One significant known advantage of proton therapy is it provides superior dose distribution with minimal exit dose compared to other forms of radiation therapy, such as x-ray therapy. There is a significant reduction of dose to organs at risk (OAR) because of the minimal exit dose. Further advantages include lower dose per treatment, which lowers the risk of side effects and may improve quality of life during and after proton therapy treatment.

One method of providing proton therapy is to use a broad proton beam, such as a spread-out Bragg peak that provides a uniform beam having multiple energies. If various energy fields are to be used to treat the patient, it may not be accomplished using a broad beam. For example, a broad beam requires an ion beam compensator per treatment field customized per patient. This means there would be one compensator required for every angle, therefore, multiple compensators would have to be used to treat a patient. For instance, for at least every 4 degrees, a different compensator would have to be used. Treatment would have to be stopped and started using 90 different ion compensators to provide a 360 degree rotational proton radiation therapy. Another issue with using a broad beam is there is an undesired shape to the dose at the proximal edge of the targeted tumor.

Definitions

A spot is a location that is configured to a diameter of a beamlet that is to be delivered to that location.

A beamlet comprises a stream of particles having a nominal diameter delivered at a predetermined rate to a starting point and to an ending point.

A line segment is configured to uniformly deliver a plurality of particles between a starting position and an ending position.

Overview

In one approach, a method of delivering a particle beam from a continuously rotating gantry towards a target, where the particle beam is composed of a plurality of beamlets. An illustrative example of such a method includes determining a plurality of predefined spots on the target, configuring the predefined spots into at least a set of smaller spots on the outside of the target and configuring a set of larger spots on the inside of the target, delivering the particle beam in a rotational pattern from the inside of the target to the outside of the target and then from the outside of the target back towards the inside of the target, where the particle beam has an inside edge of the arc it subtends, an outside edge of the arc it subtends, and central component. Finally the method optimizes the delivery of the rotating particle beam such that the inside edge and the outside edge of the arc of the rotating beam occur when the particle beam is delivered to the spots located at the center of the target, and the central component of the arc of the beam occurs when the particle beam is delivered to the spots located at the outside of the target.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

FIGS. 12A-12B illustrate positioning errors when using spiral spot delivery, in accordance with an embodiment.

Figure 1:
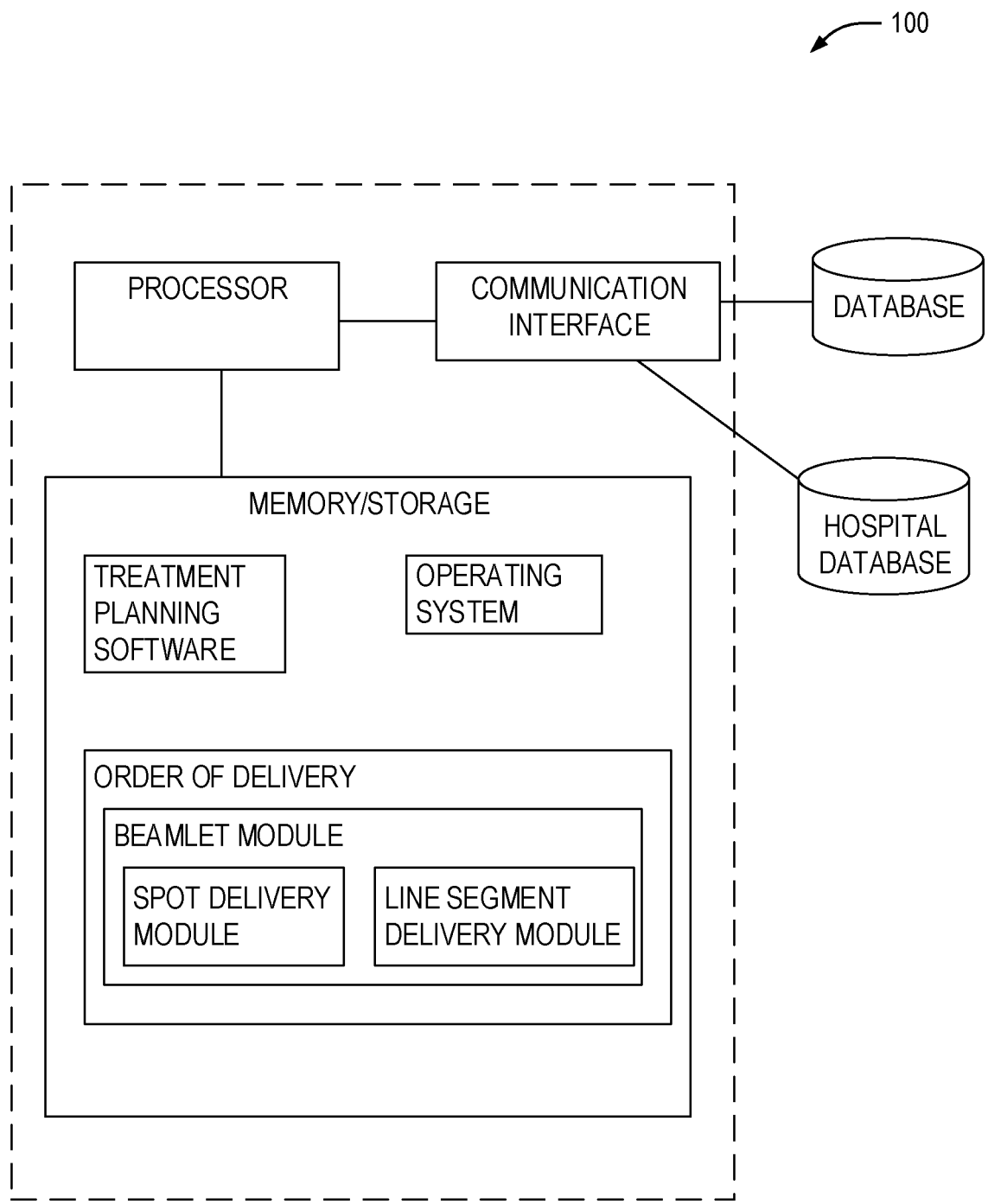
FIG. 1 illustrates generally an example of a system, such as may include a particle therapy system controller, in accordance with an embodiment.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Systems and methods described herein provide radiation therapy to a patient. The radiation therapy is provided with a rotating gantry, for example by a particle beam affixed to the gantry. The gantry may continuously rotate while the particle beam applies a plurality of beamlets. The beamlets may be applied in a spiral pattern on a target (e.g., a tumor or a portion of a tumor or other spot). In an example, rotating the gantry while delivering the particle beam may be inefficient (e.g., if dosage and penetration information for every degree or half degree is planned). In another example, rotating the gantry may introduce errors (e.g., if every few degrees are planned, such as every five or ten degrees). There are a number of advantages of providing rotational proton radiation therapy. First, instead of an undesired entrance dose at a small number of angles, the dose may be delivered from many angles.

The systems and methods described herein account for both of these issues by introducing a spiral pattern for delivery of the beamlets. The spiral pattern may be used with planned angles at a range of degrees (e.g., five, ten, fifteen, etc.). In an example, the spiral pattern may include delivering the particle beam to a central portion of the target when at a highest error and to an outer portion of the target when at a lowest error. The amount of error may depend on angle difference between the actual gantry angle and the planned angle, for example with a higher error corresponding to a larger difference between angles, and a lower error corresponding to a smaller difference between angles.

In an example, a spiral pattern for applying a particle beam to a target may decrease time needed to complete a radiation therapy treatment. For example, beamlet size of beamlets delivered during the treatment may vary. To change size of the beamlets may cause disruption to treatment, for example by taking time or using energy. Using a raster type pattern may require multiple changes in beamlet size. Using the spiral pattern may allow for as few as a single change in beamlet size. For example, smaller beamlets may be used on an outside edge of a target, while larger beamlets may be used on an inside portion of the target.

FIG. 1 illustrates generally an example of a system 100, such as may include a particle therapy system controller, in accordance with an embodiment. The system 100 may include a database or a hospital database. The particle therapy system controller may include a processor, communication interface, or memory. The memory may include treatment planning software, an operating system, or a delivery controller. The delivery controller may include a beamlet module for determining or planning spot delivery (e.g., using a spot delivery module) or line segment delivery (e.g., using a line segment delivery module).

In an example, the spot delivery module or the beamlet module may be configured to plan size of beamlets, location of a target or spot, or the like. The beamlet module may be used to determine an order of delivery of beamlets, for example in a spiral pattern as described herein. The order of delivery module may be in communication with the treatment planning software for planning delivery of beamlets. For example, the treatment planning software may be used to determine or plan gantry angle, gantry speed, beamlet size, spiral pattern (e.g., clockwise or counterclockwise), angle range for a particular spiral pattern (e.g., every ten degrees of the gantry rotation), or the like.

The processor may implement the plan, such as by communicating, via the communication interface or otherwise, to components used to implement the plan (e.g., to control devices or components, such as those described below with reference to FIG. 3). In an example, the communication interface may be used to retrieve stored information from a database or a hospital database (e.g., patient information, past procedure information for the patient or other patients, procedure instructions, information about particular devices or components, or the like).

Figure 2:
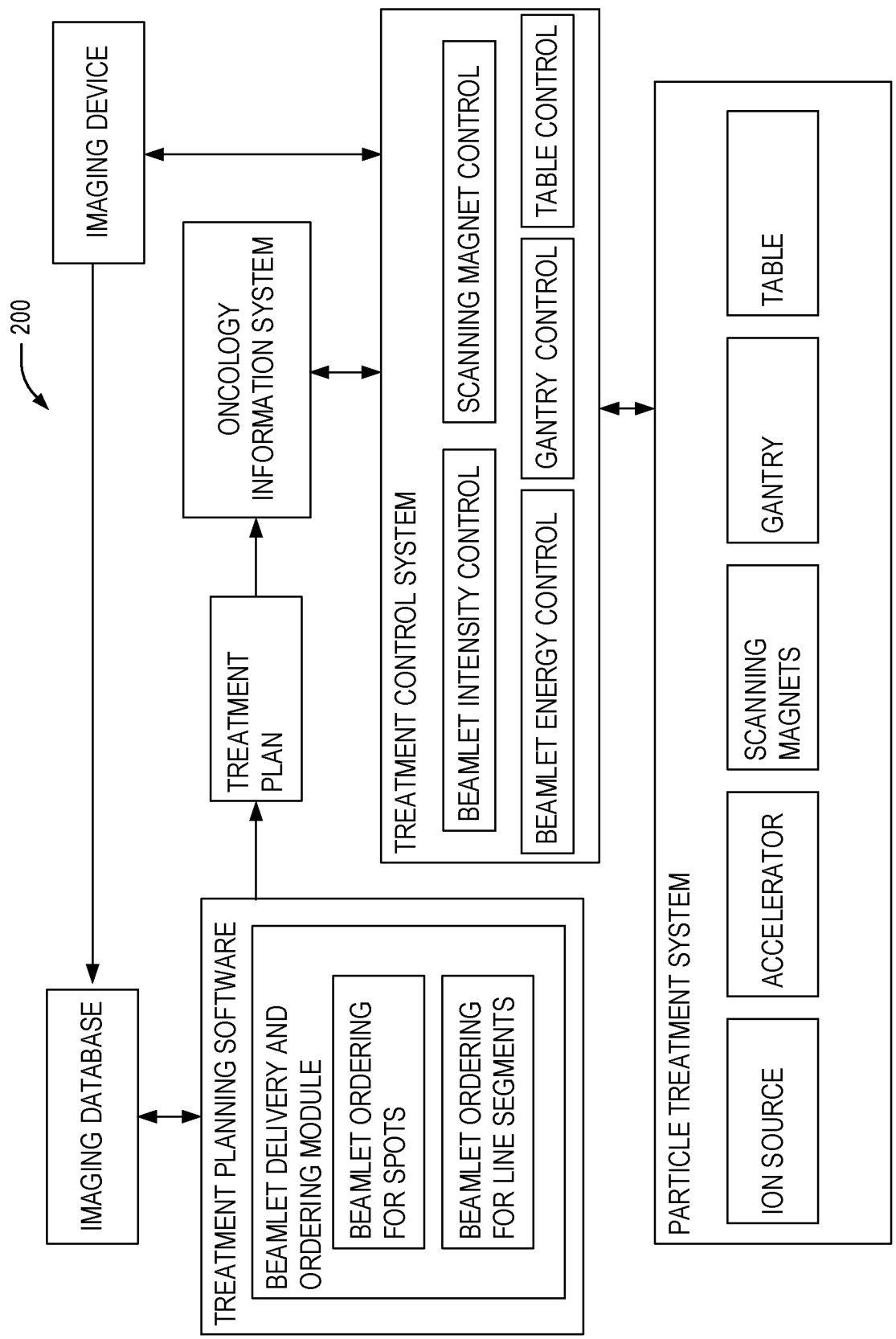
FIG. 2 illustrates generally an example of a radiation therapy system, such as may include a particle treatment system and an imaging acquisition device, in accordance with an embodiment.

FIG. 2 illustrates generally an example of a radiation therapy system 200, such as may include a particle treatment system and an imaging acquisition device, in accordance with an embodiment. The particle treatment system includes an ion source, an accelerator, and scanning magnets, each of which is described in more detail below with respect to FIG. 3. The particle treatment system includes a gantry and a table, where the gantry may be mounted on the table, affixed to the table, or stabilized with respect to the table. The table may hold a patient. The gantry may be a rotating gantry, and may rotate with respect to the table (e.g., around the table) or with respect to the patient (and the table or a portion of the table may rotate with the gantry).

The particle treatment system may communicate with a treatment control system, which may be used to control actions of the particle treatment system. The treatment control system may communicate with an imaging acquisition device (e.g., to receive images taken by the imaging acquisition device or an imaging database) or an oncology information system. The oncology information system may provide treatment plan details to the treatment control system, such as received from treatment planning system. The treatment control system may use the treatment plan to control the particle treatment system (e.g., activate the gantry, the ion source, the accelerator, the scanning magnets, a particle beam, or the like). The treatment control system, for example, may include a beamlet intensity control, a beamlet energy control, a scanning magnet control, a table control, a gantry control, etc. In an example, the beamlet intensity control and the beamlet energy control may be used to activate a beamlet of a particular size or to target a particular location. The scanning magnetic control may be used to deliver beamlets according to the treatment plan, for example in a spiral pattern. The gantry control or the table control may be used to rotate the gantry.

The treatment planning software may include components such as a beamlet delivery and ordering module, with, for example, separate controls for beamlet ordering for spots or line segments. The treatment planning software is described in more detail above with respect to FIG. 1. The treatment planning software may access an imaging database to retrieve images or store information. When a treatment plan is completed, the treatment planning software may send the plan to an oncology information system for communication with the treatment control system.

Figure 3:
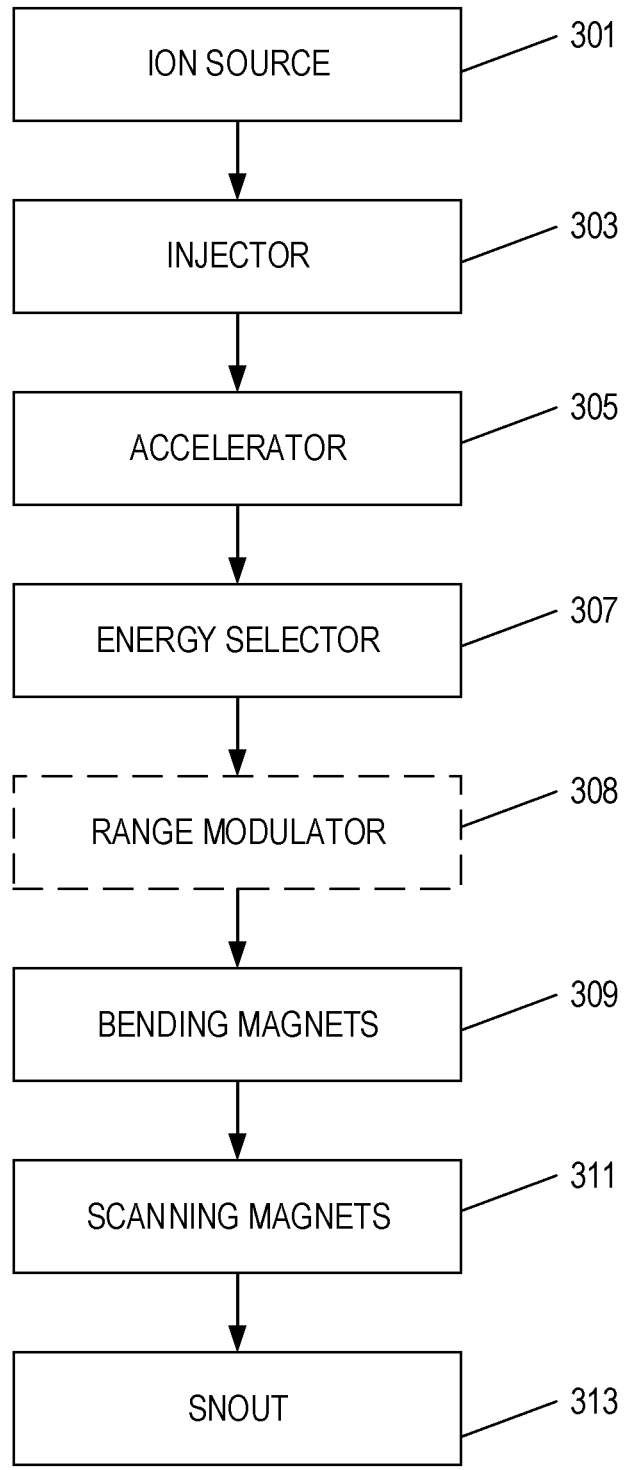
FIG. 3 illustrates generally a particle treatment system that may include a radiation therapy output configured to provide a proton therapy beam, in accordance with an embodiment.

FIG. 3 illustrates in an embodiment of a particle treatment system 300 that may include a radiation therapy output configured to provide a proton therapy beam. The particle treatment system 300 includes an ion source 301, an injector 303, an accelerator 305, an energy selector 307, a plurality of bending magnets 309, a plurality of scanning magnets 311, and a snout 313.

The ion source 301, such as a synchrotron (not shown) may be configured to provide a stream of particles, such as protons. The stream of particles is transported to an injector 303 that provides the charged particles with an initial acceleration using a Coulomb force. The particles are further accelerated by the accelerator 305 to about 10% of the speed of light. The acceleration provides energy to the particles, which determines the depth within tissue the particles may travel. The energy selector 307 (e.g., a range scatter) may be used to select the energies of the protons to be delivered to the patient. In an embodiment called passive scattering, an optional range modulator 308 (e.g., also called a ridge filter or a range modulation wheel) may be utilized to broaden the beam to fit the tumor. After selecting energies, a set of bending magnets 309 may be utilized to transport the stream of protons into a radiation therapy treatment room of a hospital. Further, scanning magnets 311 (e.g., x-y magnets) are used to spread the proton beam to, or trace, an exact image of the tumor shape. A snout 313 is used to further shape the proton beam. In various embodiments, the stream of particles may be composed of carbon ions, pions, or positively charged ions.

Figure 4:
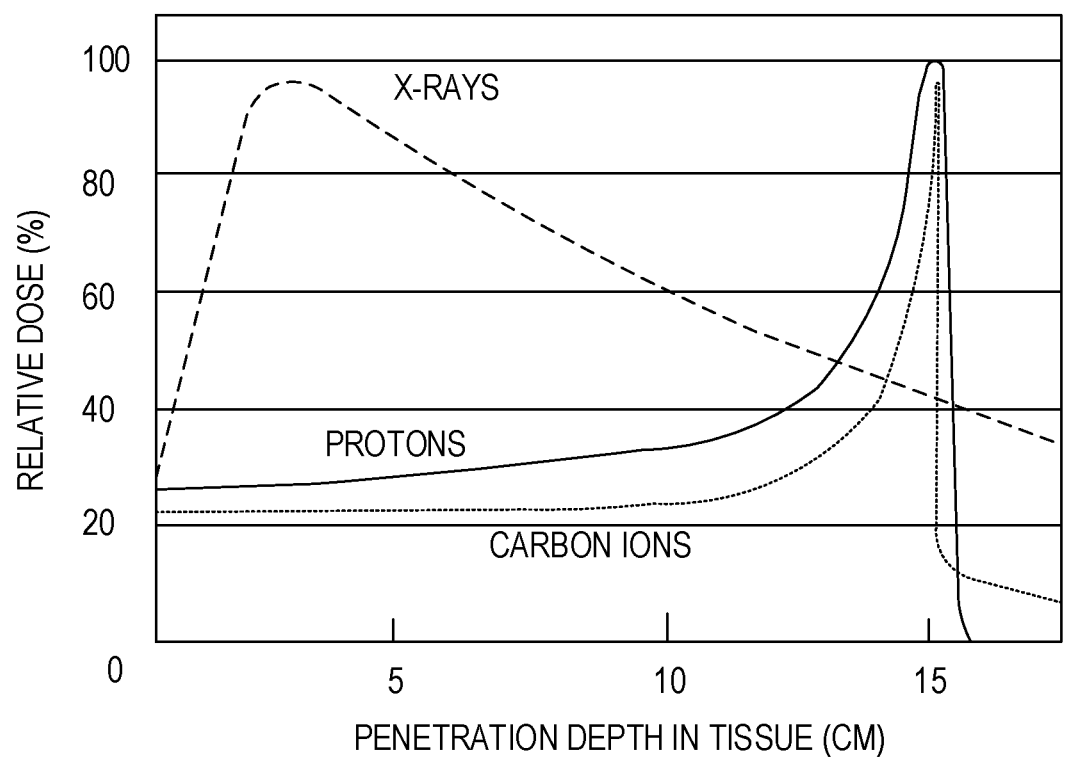
FIG. 4 illustrates generally radiation dose depths in human tissue for various types of particles, in accordance with an embodiment.

FIG. 4 provides an illustration of a comparison of radiation dose depths for various types of particles in human tissue. As shown, the relative depth of penetration into human tissue of photons (e.g., x-rays) versus protons versus carbon ions is provided (e.g., including any radiation dose provided at a distance beneath the surface, including secondary radiation or scatter). Each radiation dose is shown relative to the peak dose for a proton beam having a single energy which has been set to 100%.

The mono-energetic (e.g., single energy) proton beam indicates a plateau region starting at approximately 25% that gradually increases until approximately 10 cm depth in tissue where it rapidly increases to the Bragg Peak at 15 cm and then advantageously falls to zero within a short distance. No additional dose is delivered at the end of the Bragg peak.

The photon beam (e.g., labelled as X-rays) indicates the initial build up due to electron scatter (e.g., the primary means by which X-rays deliver dose to tissue is through transfer of energy to electrons in the tissue). This is followed by an exponential fall off, which continues past the distal edge of the target, which is at approximately 15 cm depth in the diagram. The x-ray beam has an entrance (skin) dose set to match that of the proton beam. With normalization (e.g., scaling) at 15 cm depth, the dose due to x-rays is at 40% of the dose provided by proton beam, while the x-ray beam has a peak dose of greater than 95% ("near" 100%) at approximately 3 cm depth. If the x-ray data is renormalized to achieve 100% dose at 15 cm, the peak dose at approximately 3 cm depth would be approximately 240%, in a location where dose is not desired (e.g., prior to the target). Therefore, with x-rays, a considerable amount of dose is delivered prior to the target and an appreciable amount of dose is delivered past the target.

The mono-energetic carbon beam shows a plateau region at the entrance dose that is lower than the proton beam. The carbon beam has a sharper Bragg Peak that falls more precipitously than the proton beam, but the carbon beam has a tail (e.g., known as a "spallation tail", where some of the Carbon nuclei shatter in to Helium ions) that has approximately 10% additional dose, or less, past the desired target by several centimeters. The carbon ion beam has an undesired entrance and skin dose compared to the proton beam, but the carbon ion beam has a non-trivial dose delivered past the target.

Figure 5:
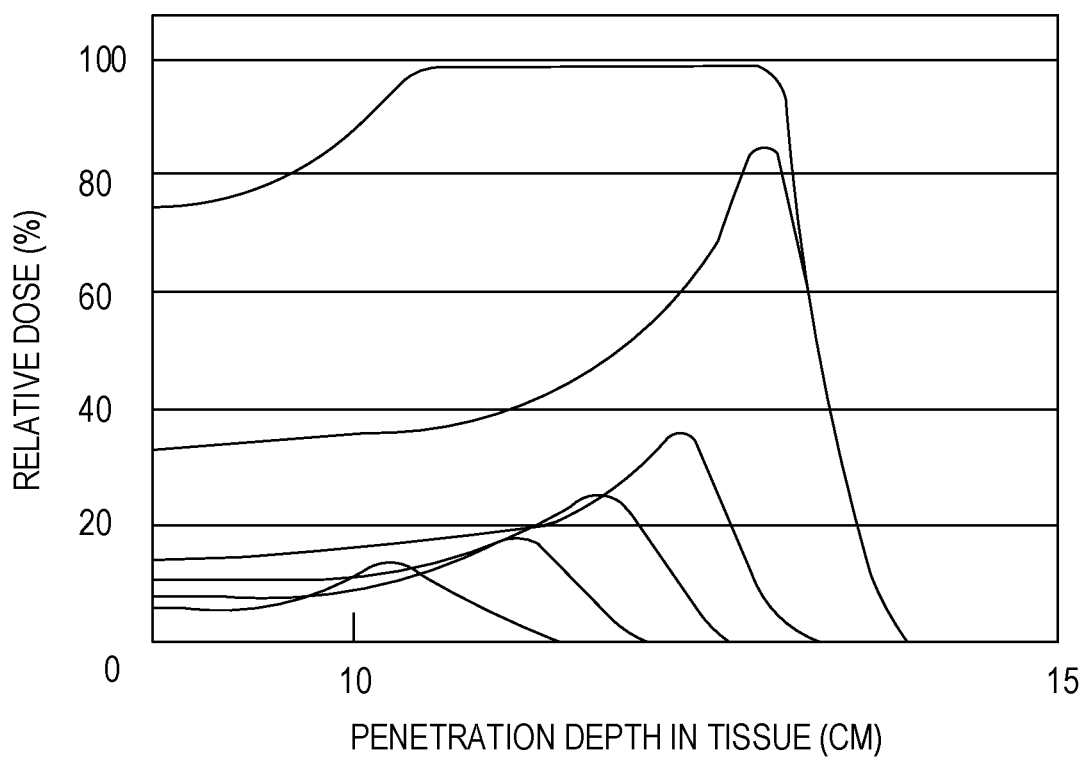
FIG. 5 illustrates generally a spread out Bragg Peak, in accordance with an embodiment.

FIG. 5 provides an illustration of a spread-out Bragg peak (SOBP). The SOBP. displays a relative depth dose curve for the combination of a set of proton beams of various initial energies each of which has had some spread in energy (e.g., variable absorption of energy in tissue). The desired result of having a uniform dose for a target of a particular thickness. As shown, the target is shown with a proximal depth of approximately 10 cm, a distal depth of approximately 13 cm, and a target thickness of approximately 3 cm. Within the target, the dose is quite uniform (with an average normalized at 100%). The diagram does not start at 0 cm depth and is not explicitly showing the entrance (skin) dose, but the nature of the entrance region of proton beams is a relatively flat depth dose curve. Typically, the entrance (skin) dose will be approximately 70% of the target dose (e.g., shown at the far right edge of the x-axis). A SOBP may be obtained using a variety of approaches, including using a scattered proton beam with modulation of the energy (variable absorption) utilizing a variety of devices (e.g., a static ridge filter or a dynamic range modulation wheel), or by selection of a number of mono-energetic proton beams that do not undergo scatter.

Figure 6:
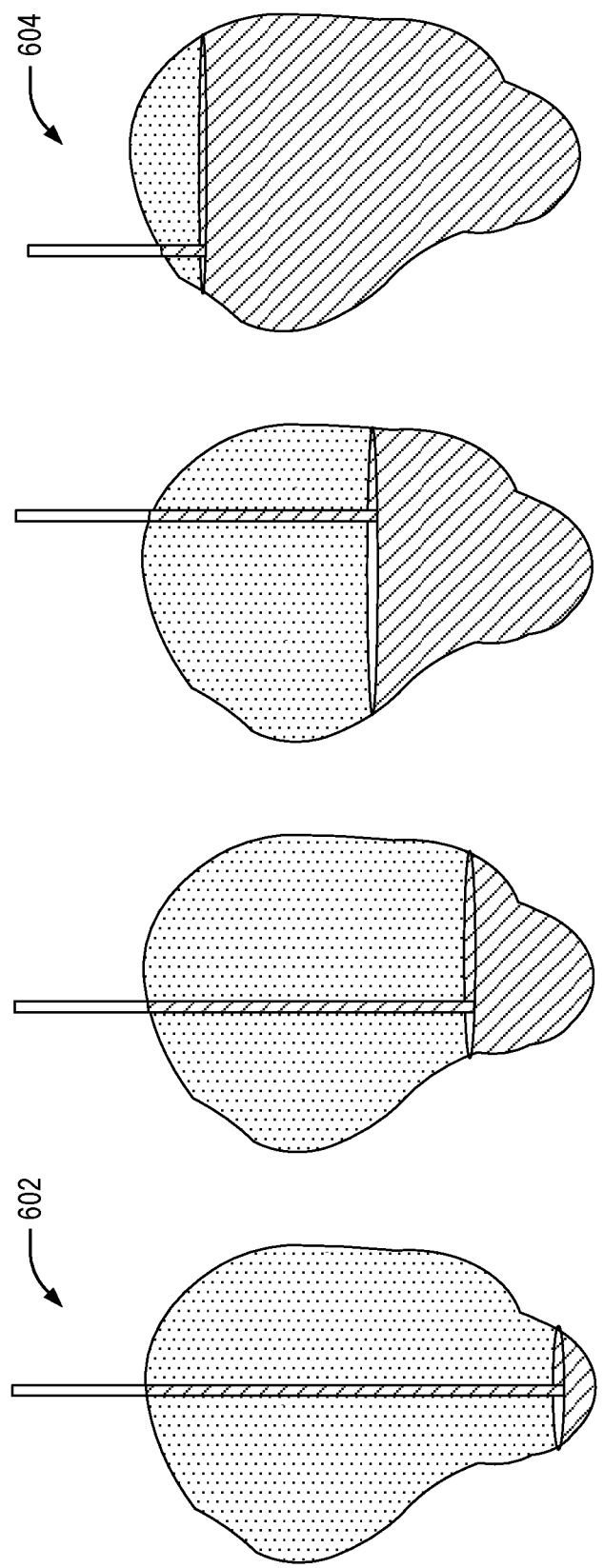
FIG. 6 illustrates generally pencil beam scanning of an irregular shape volume from distal edge to proximal edge, in accordance with an embodiment.

FIG. 6 provides an illustration of a Pencil Beam Scanning of an irregular shape volume from a distal edge (e.g., bottom) to a proximal (e.g., top) edge. As shown, the irregular shaped tumor volume is irradiated layers of protons. For example, a first time snapshot 602 shows a first layer of protons being delivered, and a later time snapshot 604 shows that most of the layers have been delivered. Each layer has its own cross-sectional area to which the protons having the same energy are delivered. The total radiation dose is provided as a layer-by-layer set of beamlets. Each layer of may have different energies. The most common means of specifying and delivering the set of beamlets to the cross-sectional area is to define and deliver beamlets having a constant diameter ("spot size") to a selection of grid points on each layer. While the majority of the dose from the beamlet is delivered to the targeted layer, a significant amount of dose is delivered along the path to the targeted layer. The dose to proximal layers from beamlets defined for distal layers is accounted for in the specification of the beamlets defined for the proximal layers. The ability to individually specify the number of particles (e.g., the meterset) for a given beamlet ensures that each part of the volume being irradiate receives the desired dose.

Figure 7:
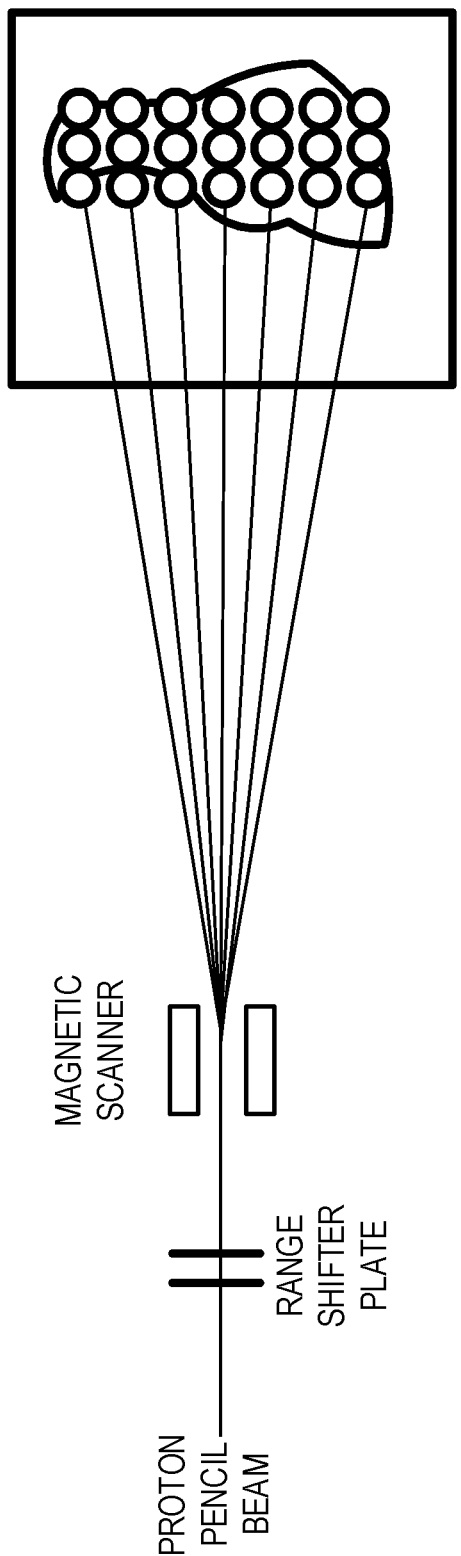
FIG. 7 illustrates generally a diagram of an active scanning proton beam delivery system, in accordance with an embodiment.

FIG. 7 provides an illustration of a diagrammatic representation of a typical active scanning proton beam delivery system. As shown, a single layer of a pencil beam scan is being delivered, with a grid of spots depicted on a patient in conjunction with a contour of the cross-sectional area to which particles are to be delivered. An incoming mono-energetic proton beamlet has a specified amount of its energy absorbed by the Range Shifter (e.g., in FIG. 7 it is a Range Shifter plate), resulting in a beamlet with the desired energy to achieve a certain depth for the Bragg Peak in the patient to treat the specified layer. A magnetic scanner, which has the ability to deflect the particles in both a vertical and a horizontal direction. The strength of the magnetic fields may be adjusted to control the deflection in the direction perpendicular to the magnetic field and the incoming beamlet. The rate at which the magnetic field strengths may be adjusted determines the rate at which the scanning may take place. For instance, the intensity of the proton beamlet in combination with the scanning rate determines how much dose may be delivered to a specific area (e.g., in FIG. 7, a "spot") in a particular amount of time (e.g., particles/unit area). In theory, the magnetic field strengths may be adjusted independently of each other (in a fashion similar to the children's toy "Etch a Sketch®", provided by Spin Master™, Toronto, Canada; with the pencil beamlet intensity being a variable not available in the children's toy). The most common scheme for scanning is to scan in one direction quickly and to scan in the perpendicular direction more slowly in a raster fashion, similar to how early televisions were controlled (e.g., Cathode Ray Tube (CRT), which use electrons instead of protons), but arbitrary patterns may be scanned (similar to the previously mentioned toy). Delivery of distinct spots is achieved by incrementing the scanning magnetic field strength and throttling the pencil beam intensity between increments.

Figure 8A:
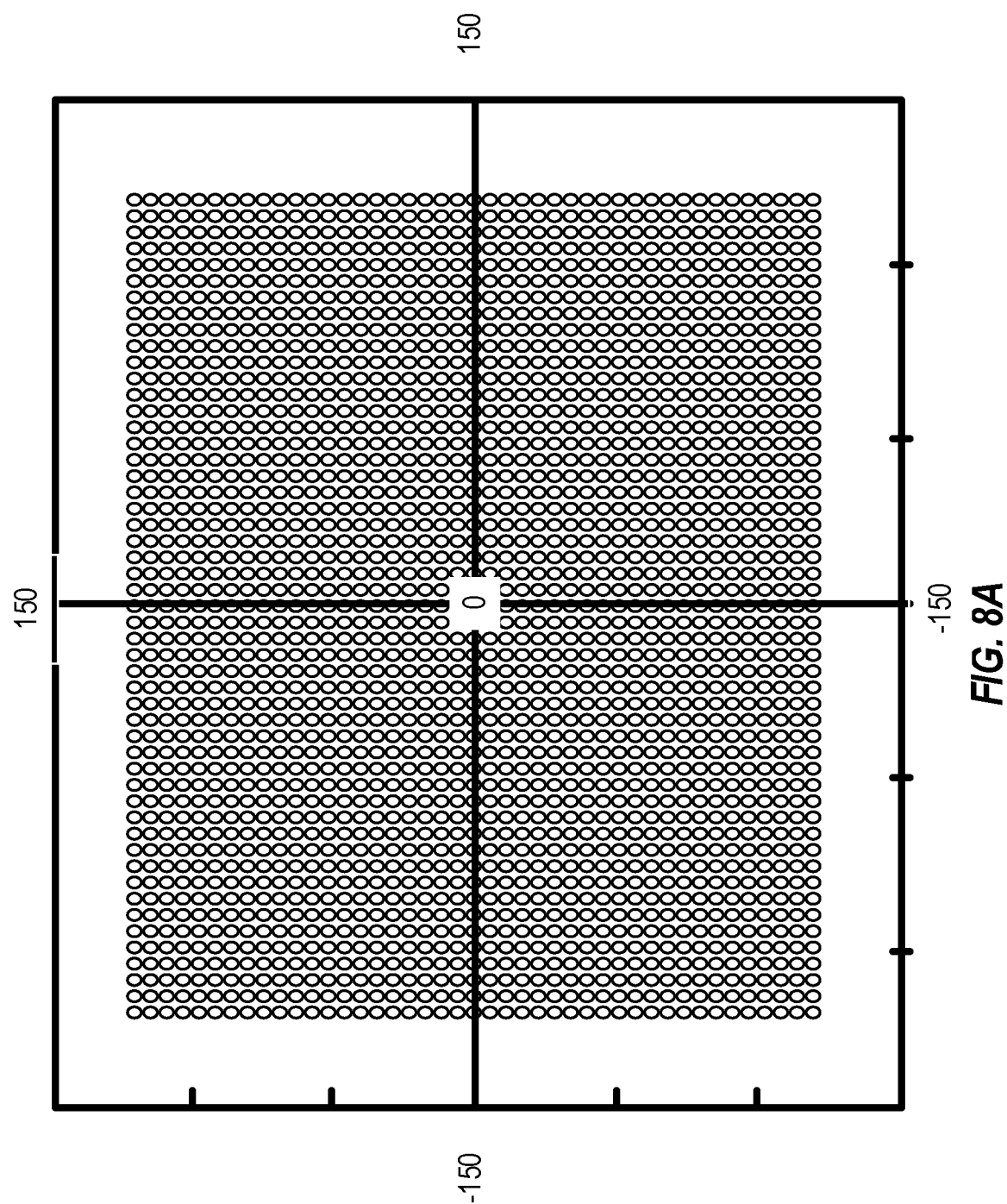
FIGS. 8A-8C illustrate generally a beamlet delivery system as stationary spots, in accordance with an embodiment.
Figure 8B:
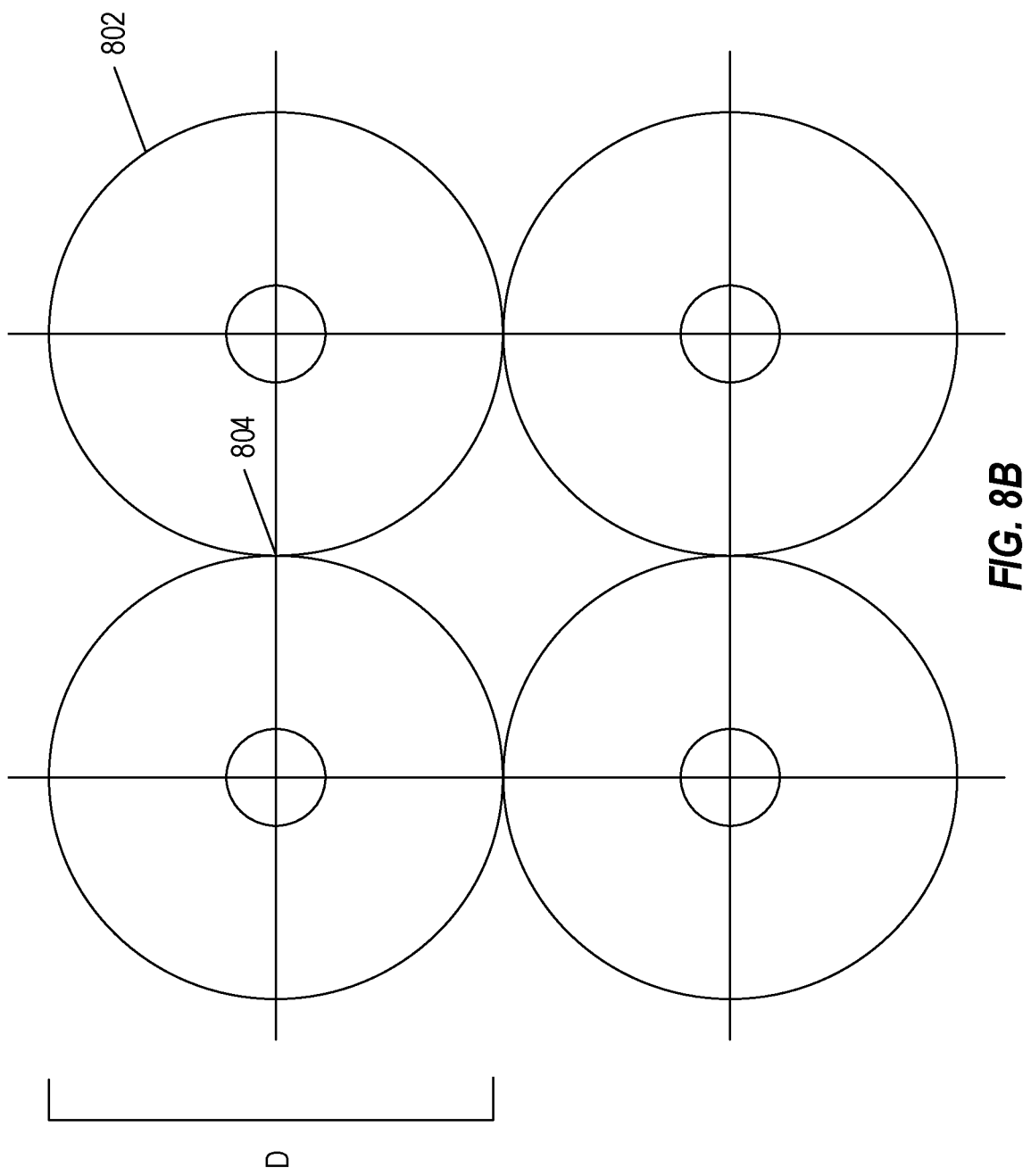
Figure 8C:
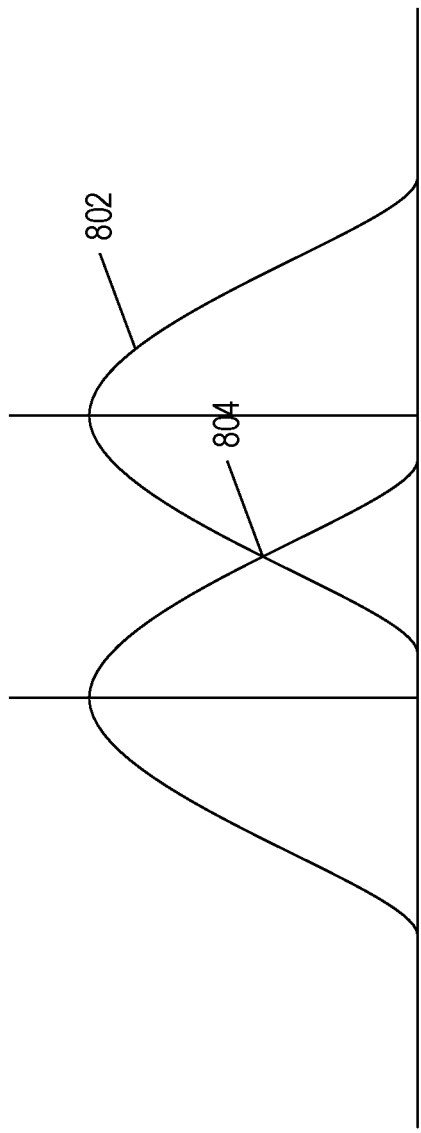

FIGS. 8A-8C illustrate generally a beamlet delivery system as stationary spots, in accordance with an embodiment. For illustrative purposes, when delivering beamlets to stationary spots, the spots are adjacent to one another on a Cartesian grid. The spots are nominally circular in shape having a size parameter (e.g., nominally a diameter) roughly equal to the grid spacing. In practice, spots are located next to one in a grid layout such that the edges of each spot abut against one another. The spot size diameter may be selected by the user based on machine capabilities. In an embodiment, small spots range from 2-4 millimeters, and large spots range from 8-12 millimeters in diameter. In an embodiment a small spot may be 3 millimeters, and a large spot may be 10 millimeters in diameter. As shown in FIG. 8A, the spots may be arranged as having an ellipsoid shape of approximately about 2 millimeters of the semi-minor axis and about 5 millimeters on the semi-major axis. For this particular example, the delivery of a set of beamlets may be provided at distinct spacing of 5 mm in both x-y directions.

FIG. 8B illustrates a grid having four adjacent spots, each spot (e.g., spot 802) having the same diameter D with radius ½D. The intensity pattern (e.g., particles delivered per unit volume) at a spot in practice may be approximated as a Gaussian function, as shown in FIG. 8C, which illustrates a Gaussian distribution of radiation dose, full width-half max. The size parameter (e.g., diameter) of the spot defines a "Full Width at Half Max" of the peak intensity at the center of two adjacent spots.

With a size parameter equal to the grid spacing, the beamlets delivered to adjacent spots overlap. A point 804, which is equidistant between spot A and spot B, for example, has a summed intensity (e.g., number of particles per unit area) with half the Gaussian distribution contributed by each spot (or, a volume when considering all three x-y-z dimensions). If the spots are of equal meterset (e.g., the same number of particles being delivered to every spot), the point 804 equidistant between spot A and spot B has the same intensity as the centers of the adjacent spots because of the summed intensity. This results in a highly uniform plane of dose delivery.

Figure 9:
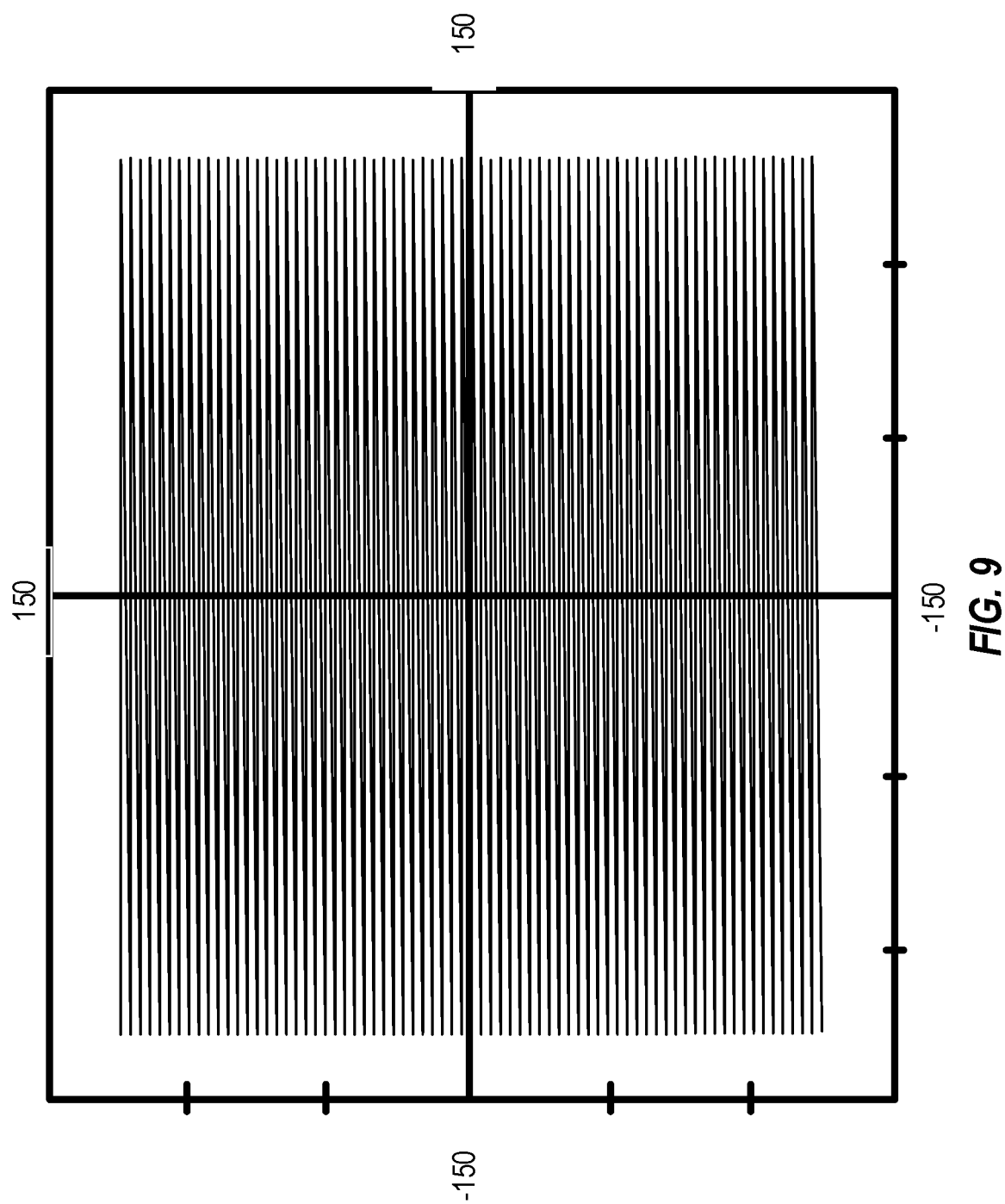
FIG. 9 illustrates generally a beamlet delivery system as line segments, in accordance with an embodiment.

FIG. 9 provides an illustration of beamlet delivery as line segments. The delivery mode of line segments of particle beamlets sometimes referred to as line scanning is a type of scan mode that is linear. Each beamlet that is delivered to the target has a starting point and an ending point. As illustrated, a beamlet is continuously scanned from a spot on the right to a spot on the left. The size and spacing of the line segments allow for a uniform dose delivery. The scanning may be controlled in any combination of continuous and/or incremented fashion, and independently control the particle beamlet intensity, generating an arbitrary pattern.

A proton broad beam, such as one created using scattering and utilizing a spread-out Bragg peak, provides a beam delivering relatively uniform dose to the entire target volume. If many fields are to be used to treat the patient, it may not be accomplished using proton broad beams. For example, a broad beam requires an ion block and an ion beam compensator per treatment field customized per patient. This means there would be one block and one compensator required for every angle, therefore, multiple blocks and compensators would have to be used to treat a patient. For example, for at least every 4 degrees, a different block and a different compensator would have to be used. A system would have to stop and start treatment using 90 different ion blocks and 90 different ion compensators to provide a 360 degree rotational proton radiation therapy. Even if a system used a multi-leaf collimator instead of ion blocks, the system would still need to use ion compensators. Another issue with using a broad beam is there is an undesired shape to the dose at the proximal edge of the targeted tumor due to the use of the ion compensator.

Figure 10A:
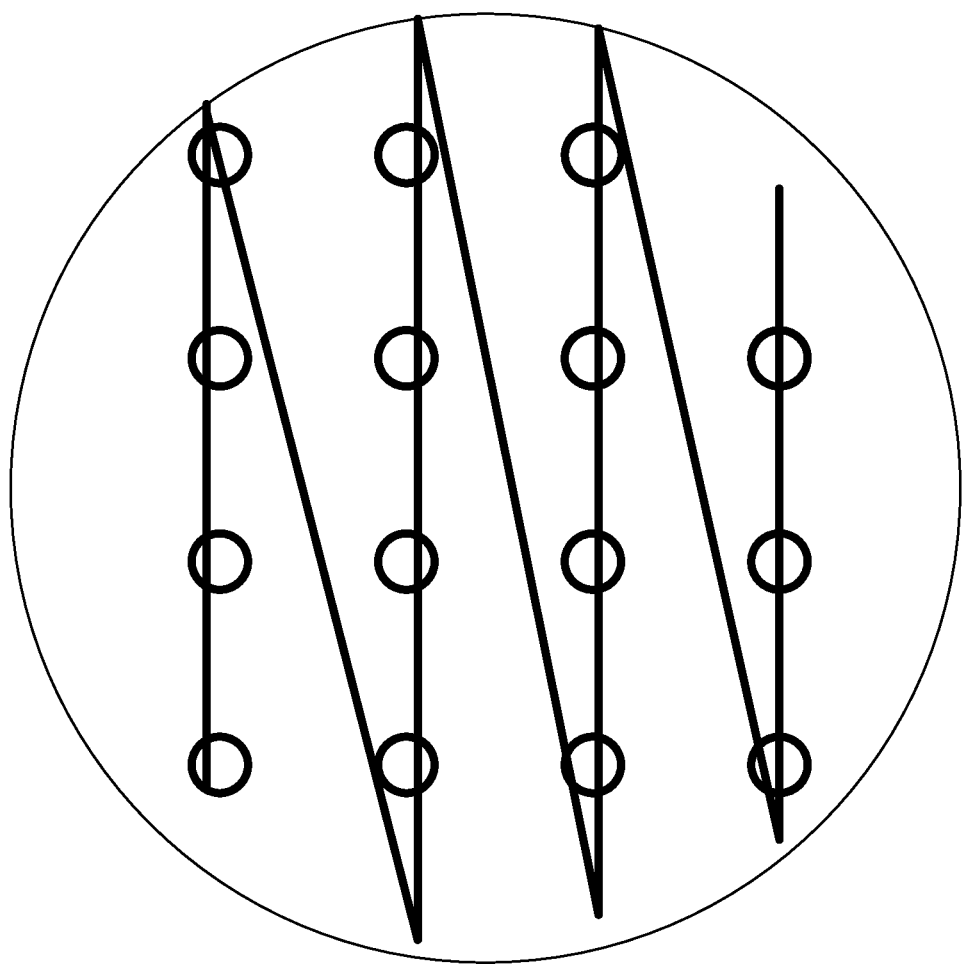
FIG. 10A illustrates generally a linear spot delivery path on a grid, in accordance with an embodiment.

FIG. 10A illustrates generally a linear spot delivery path on a grid, in accordance with an embodiment. One form of particle therapy is spot-scanning. Spot-scanning allows for the delivery of complex dose distributions. With a rotating gantry, there are issues of spot placement of a particle beam because the spots are not delivered instantaneously, and as the gantry moves, the spots are delivered at an angle that is not exactly the planned nominal gantry angle. The system must deliver a plurality of beamlets, deliver using a certain particle energy, at a particular gantry angle, while the gantry rotates constantly at a nominally fixed rate (to avoid vibration and flexing). This must be accomplished to accurately reflect what was planned in the radiation therapy treatment plan, if the planning assumes a sampling of individual angles. The linear spot delivery path using a raster pattern shown in FIG. 10A illustrates one approach that may result in errors as the gantry rotates.

The raster pattern approach to treatment planning assumes that a plurality of beamlets will be delivered from a single angle constituting a static beam. More than one static beam may be defined as part of a treatment plan. To utilize existing treatment planning systems, proton arc therapy must be modelled as being delivered from a set of angles rather than a continuum of angles. While a system may attempt to model the delivery of each beamlet from a distinct angle during rotation, the added complexity, including machine specific behavior that might vary, from day to day makes this approach impractical. In practice, the delivery of the plurality of beamlets associated with a planned angle is delivered from the midpoint between the current planned angle and the previous planned angle through the current planned angle until the midpoint between the current planned angle and the next planned angle (potentially wrapping to the angle 360 degrees from the first/initial planned angle of the beginning of the arc).

Figure 10C:
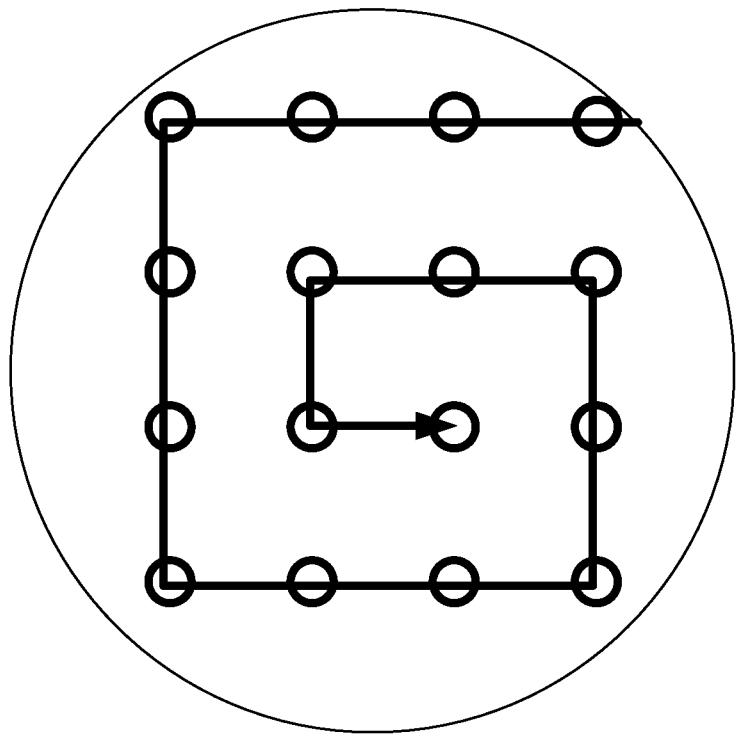
FIGS. 10B-10C illustrate generally spiral delivery paths on a grid, in accordance with an embodiment.
Figure 10B:
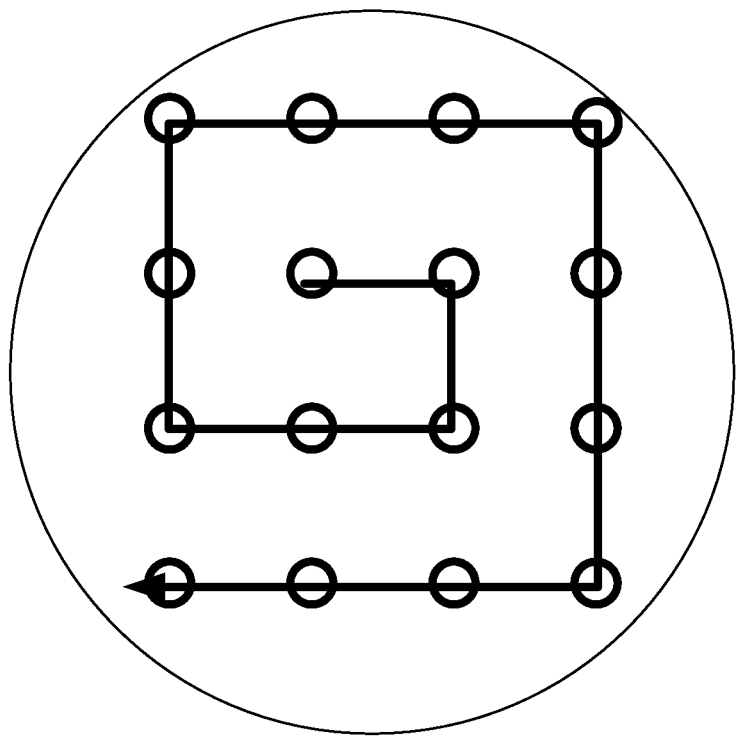

FIGS. 10B-10C illustrate generally spiral delivery paths on a grid, in accordance with an embodiment. The spiral patterns shown in FIGS. 10B-10C minimize the errors resulting from a rotating gantry. The spiral patterns shown improve target accuracy and decrease radiation outside the target compared to the raster pattern shown in FIG. 10A while the gantry rotates.

The systems and methods described herein use proton arc therapy to optimize a radiation dose when delivering protons to certain spots. When delivering to certain spots, discrepancies may be minimized for what was planned versus what is actually delivered using the spiral pattern scan described herein. Unless the spots that are further from the isocentric axis are delivered while the gantry is closest to the current planned angle, the resulting actual spot location may be far from the intended spot location and the overall trajectory of the beamlet will differ significantly from the expected trajectory. Using a spiral scan minimizes the errors in the actual spot locations and minimizes the discrepancy between the expected and actual trajectories of the beamlets.

Figure 11A:
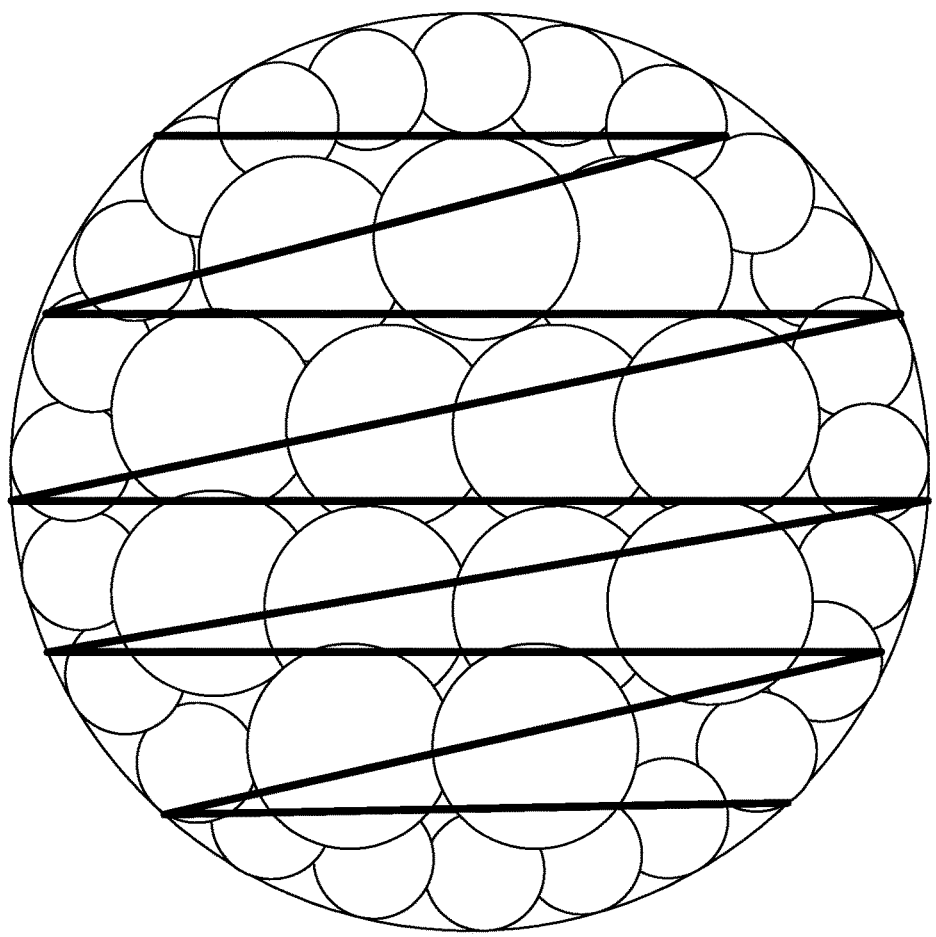
FIG. 11A illustrates a linear spot delivery path with differing spot sizes and a raster pattern, in accordance with an embodiment.
Figure 11B:
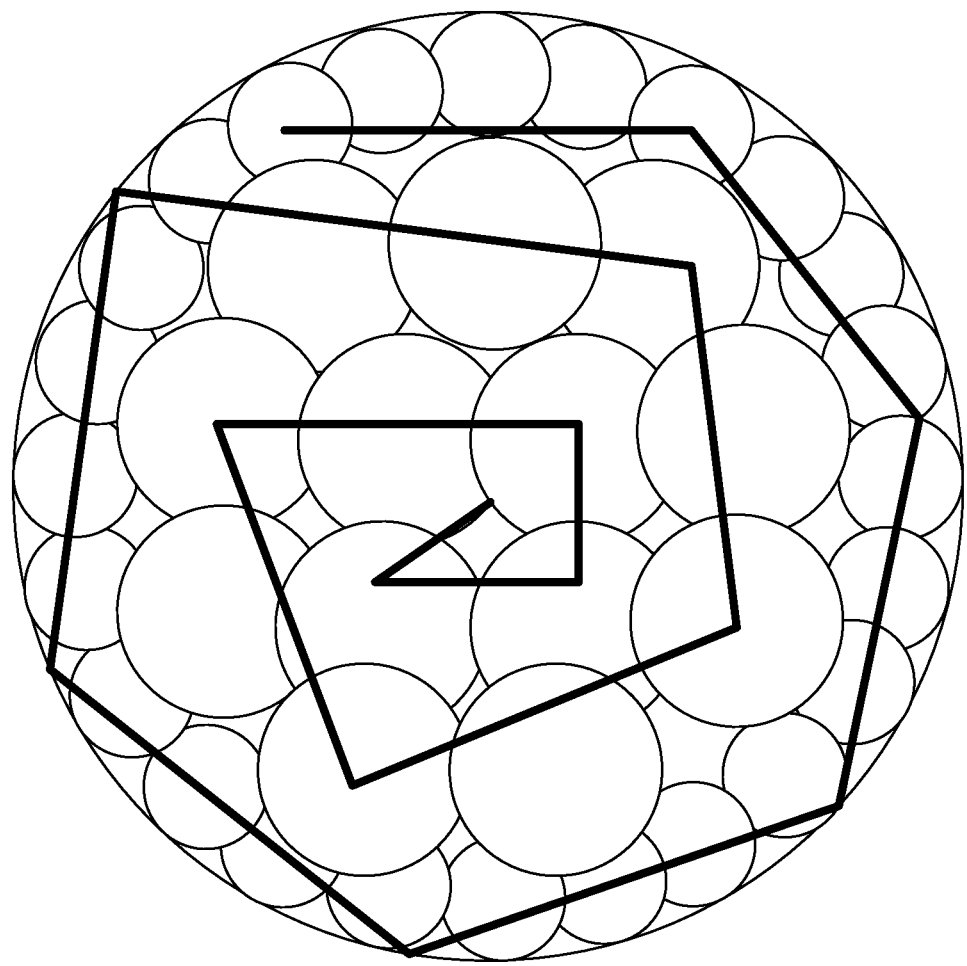
FIG. 11B illustrates a spiral spot delivery path with differing spot sizes, in accordance with an embodiment.

FIG. 11A illustrates a linear spot delivery path with differing spot sizes and a raster pattern, in accordance with an embodiment. FIG. 11B illustrates a spiral spot delivery path with differing spot sizes, in accordance with an embodiment.

The trade-off between a small and large spot is that to only deliver small beamlets to a small spot takes an inordinate amount of time to deliver radiation therapy. Therefore, to decrease the time, it is better to deliver the small beamlets to the outer edges/exterior of the tumor and deliver larger spots to the interior of the tumor. Changing spot size during delivery is a time consuming activity. When using the raster pattern of FIG. 11A for delivery of spots, any attempts to change the spot size when at the outer edges of the tumor result in a transition. As shown in FIG. 11A, each line on the grid involves two changes in spot size, resulting in dozens of transitions between spot sizes for the entire beam. By using the spiral delivery pattern shown in FIG. 11B, there may be as few as a single transition in spot sizes when going from the set of smaller spots treating the outer edges of the tumor to the set of larger spots treating the inner region of the tumor. Similarly, there may be as few as a single transition in spot sizes when going in the reverse, resulting in only two changes in spot size for the entire beam. In an example, the spiral pattern may be a two-dimensional spiral pattern, delivering dosage at each layer of the target.

In an example, beamlets may be delivered at the edges of an arc range may while the spiral is in the center of the target. For example, in an arc from 0 degrees to 10 degrees, the target may be planned as if the gantry was stationary at 5 degrees. In this example, the outside of the spiral occurs as the gantry approaches and leaves 5 degrees, while the center of the spiral occurs as the gantry leaves 0 degrees and as the gantry approaches 10 degrees. For example, starting at 0 degrees, the spiral may begin at the center of the target and spiral outward until ending (at an outward point of the spiral) around 5 degrees. Then, in an example, the spiral may reverse (e.g., move clockwise from 0 to 5 degrees, then counter-clockwise from 5 to 10 degrees, or vice versa) on the way back to the center of the target as the gantry moves from 5 to 10 degrees. The process may be repeated on a different layer of the target at another arc, for example from 10 to 20 degrees, etc., until the dose is completed.

FIGS. 12A-12B illustrate positioning errors when using spiral spot delivery, in accordance with an embodiment. FIG. 12A illustrates a positioning error 1204 according to an error angle 1202, which may be equal to a gantry angle rotation relative to a planned gantry angle. For example, for a planned angle of 5 degrees, as the gantry rotates to ten degrees, the positioning error 1204 may be at a maximum. When the gantry rotates to 5 degrees, the error may be at a minimum (or non-existent). The gantry may rotate continuously at a constant rotation speed, with a constant angular velocity. The change in position (error) may be equal to the angular velocity divided by cosine of the gantry angle. Path differences due to energy absorption (which may be minor) may be ignored, due to difficulties in determining the energy absorption of each path. To remove these errors, the particle beam may be directed at a central portion of the target when the error is highest (e.g., at positioning error 1204) to minimize the error, and the particle beam may be directed at outer portions of the target when the positioning error 1204 is lower (e.g., when closer to the central arc angle).

FIG. 12B illustrates a cross section of an irradiation layer, for example at a gantry angle of 0 degrees, which may be a circle. At other gantry angles, the cross section may be elliptical (e.g., if shown at the higher error of positioning error 1204 shown in FIG. 12A).

Error increases as distance from central planned gantry angle increases. At zero distance from the central planned gantry angle, zero error occurs. For an arc of ten degrees, for example, from five degrees before the central planned gantry angle to five degrees after the central planned gantry angle, maximum error occurs at the five degrees before and the five degrees after. This error is compounded when a raster-scan approach is used. This error is lowered, for example compared to the raster-scan approach, when a spiral pattern approach is used.

Figure 13A:
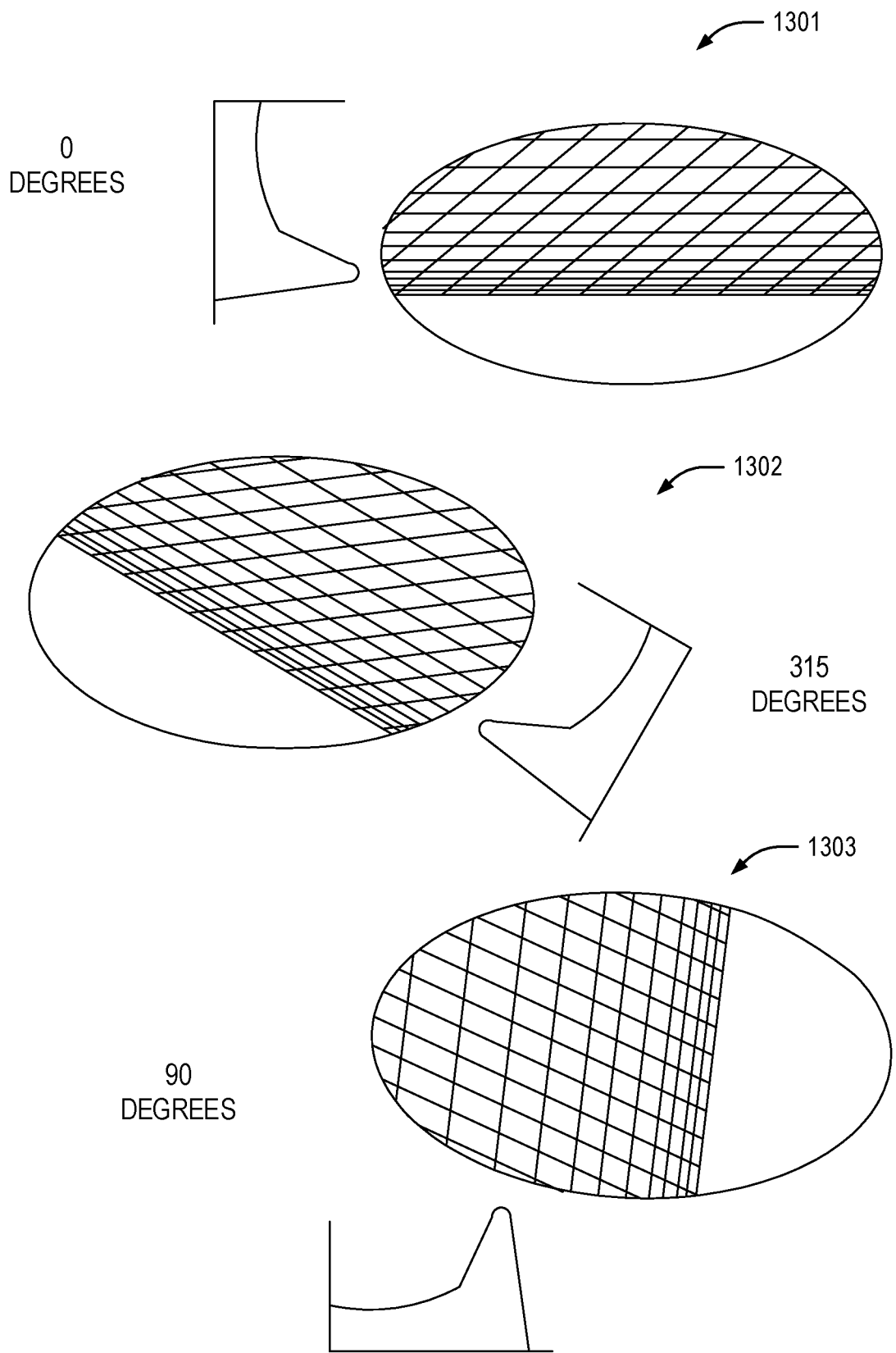
FIG. 13A illustrate arc angle target location intensity and Bragg peaks for various angles, in accordance with an embodiment.

FIG. 13A illustrates arc angle target location intensity and Bragg peaks for various angles, in accordance with an embodiment. The angles show how the penetration of the particle beam has different intensity and distance according to the angle of the gantry.

Increasing the number of angles that multiple doses to the targeted tumor may be provided allows for any given region of the body that is not a targeted tumor to receive a smaller dose. By using a large number of angles, the statistical error of stopping power as well as any error in patient positioning may be reduced because these errors may be made to cancel each other by averaging of overlapping doses. Thus, by providing a good dose distribution even in the face of errors in positioning or stopping power, the proton therapy is more robust.

The rotating gantry may compensate for increased dosage in a center of the target by using techniques such as planning the spiral to "end" and restart at somewhere other than the center of the target on that plane. As shown in FIG. 13A, different angles produce different penetration depths and by having them end at not quite the center of the target, over dosing the patient may be avoided. Decreasing the intensity of beamlets closer to the center along the line perpendicular to the isocentric line and along the direction of motion of the gantry may provide similar and more precise compensation.

Figure 13B:
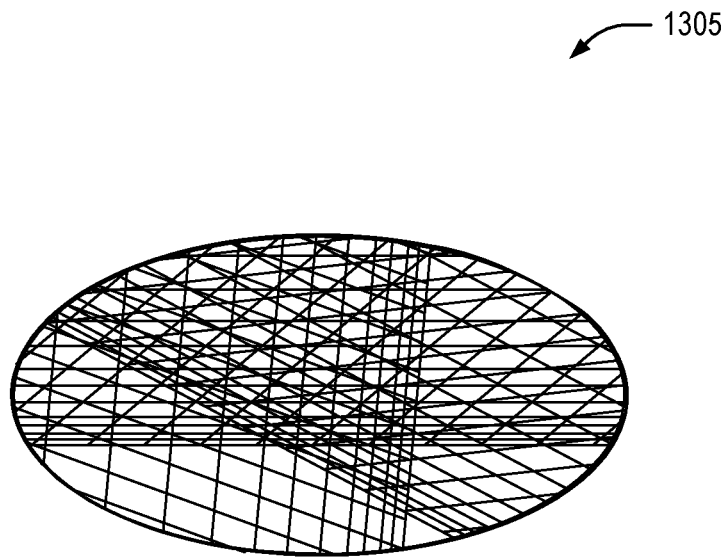
FIG. 13B illustrates a composite target location intensity, in accordance with an embodiment.

FIG. 13B illustrates a composite target location intensity, in accordance with an embodiment. The composite image shows how some overlap occurs among the different angles, but the overlap is minimized by not having all of the angles penetrate to the same depth in the target.

Proton arc therapy delivered using pencil beam scanning provides the ability to deliver distinct energies, where the change in energies may occur in less than one second. Pencil beam scanning enables intensity modulated proton therapy (IMPT), The selection of energies is very important because the selection of energies controls the depth of the radiation therapy treatment. Particle therapy inherently stops at a certain depth for a particular energy. This allows for the depth of treatment into a region of tissue to be layered. For each layer, the outline of the treatment may conform to a particular region of tissue; thereby allowing the outline to vary for the tumor from layer to layer, which is ideal for irregularly shaped tumors that are near organs at risk. When delivering from a rotating gantry there is limited time for delivering using multiple energies to distinct layers. The selection of energies at a given angle is important because it controls the depth at which the majority of the dose is delivered into the tumor. A system is able to achieve a desired aggregate dose to the tumor and do so in a timely fashion by judicious selection of a very limited number of energies for each angle. The system is able to ensure that the tumor is wholly irradiated by choosing energies that deliver past the midline of the tumor from a given angle. It is the aggregate dose to the tumor from all of the angles that is of clinical significance.

Figure 14:
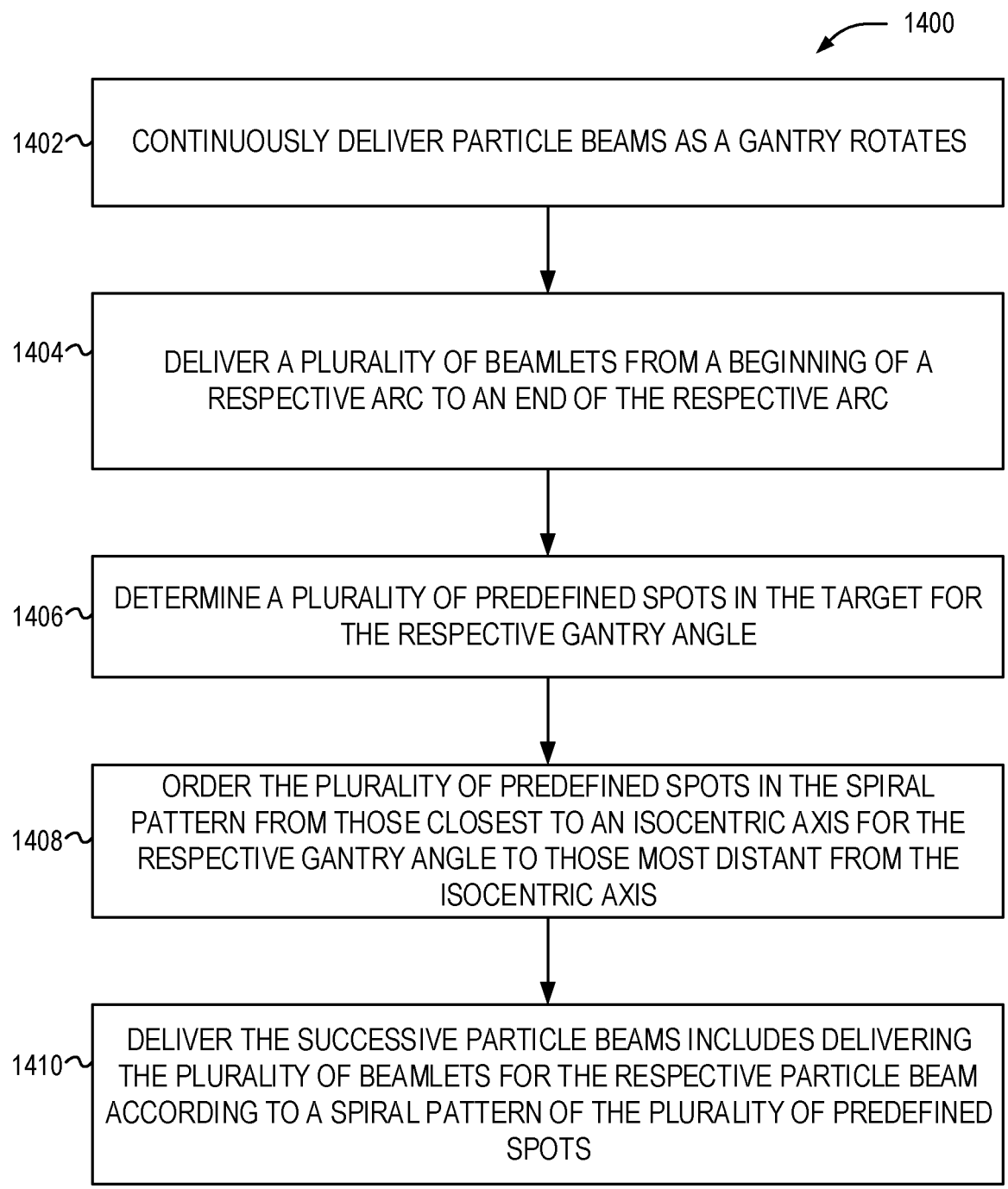
FIGS. 14-15 illustrate flowcharts showing techniques for delivering a plurality of particle beams from a rotating gantry towards a target, in accordance with an embodiment.
Figure 15:
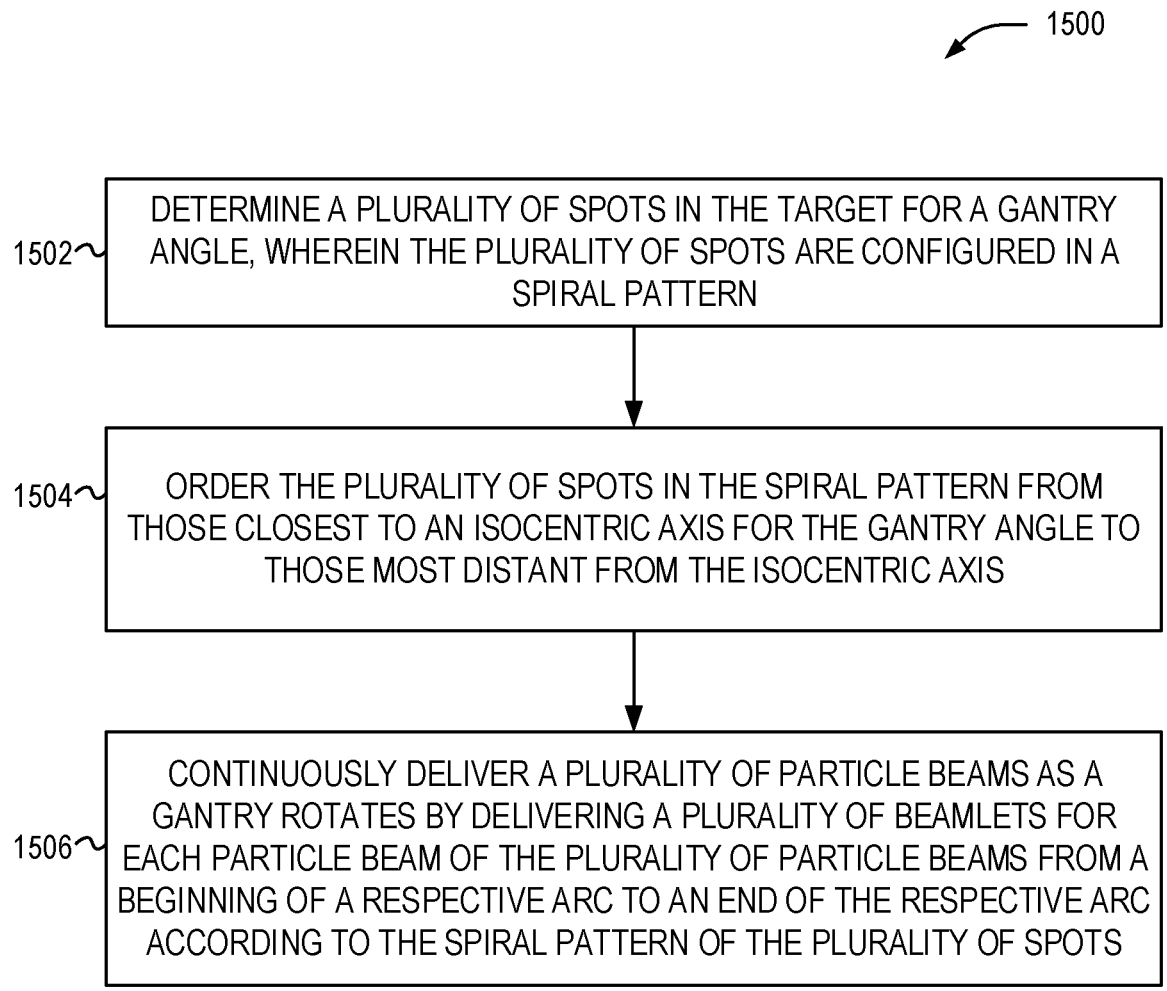

FIGS. 14-15 illustrate flowcharts showing techniques for delivering a plurality of particle beams from a rotating gantry towards a target, in accordance with an embodiment.

FIG. 14 illustrates a technique 1400, including an operation 1402 for continuously delivering a plurality of particle beams as a gantry rotates. In an example, each particle beam of the successive particle beams has an associated arc, for example with a center of the associated arc corresponding to a particular gantry angle for each particle beam. A treatment plan may be developed for the center (e.g., a central angle) of the associated arc, with the associated arc occupying a set of angles (e.g., 5 degrees, 10 degrees, 15 degrees, etc.). A particle beam may include at least one of a plurality of protons, carbon-ions, ions, pions, or positively charged particles.

The technique 1400 includes an operation 1404 for delivering a plurality of beamlets from a beginning of a respective arc to an end of the respective arc. The beamlets may be delivered from a beginning of a respective arc to an end of the respective arc. For example, for a ten degree arc starting at zero degrees, the beamlets may be delivered from zero degrees to ten degrees. In this example, the center of the respective arc may be five degrees.

The technique 1400 includes an operation 1406 for determining a plurality of predefined spots in the target for the respective gantry angle. The plurality of predefined spots may be configured in a spiral pattern. The plurality of spots may be equivalent to the beamlets (e.g., in size). The spots may be contiguously located (e.g., within the target, on a layer). In an example, spots located at an outside edge of the target may have a smaller diameter than spots located at a position inside the target (e.g., not on an outside edge or more centrally located to the target). Beamlets associated with larger diameter spots may have a greater dose than beamlets associated with smaller diameter spots. In an example, intensity modulation of the larger diameter spots is greater than the smaller diameter spots. A spot may include a location (e.g., within a layer of a target). A spot may include a diameter of a beamlet delivered to the location. In an example, a user may select a spot size for the location.

The technique 1400 includes an operation 1408 for ordering the plurality of predefined spots in the spiral pattern from those closest to an isocentric axis for the respective gantry angle to those most distant from the isocentric axis.

The technique 1400 includes an operation 1410 for delivering the successive particle beams includes delivering the plurality of beamlets for the respective particle beam according to a spiral pattern of the plurality of predefined spots. In an example, the plurality of beamlets may be delivered in a clockwise configuration followed by a counter-clockwise configuration or may be delivered in a counter-clockwise configuration followed by a clockwise configuration.

Delivering the plurality of beamlets may include delivering the beamlets from a position inside the target to a position on an outside edge of the target. Delivering the plurality of beamlets may include a single transition between spots of varying size, for example during a spiral pattern. In this example, scanning magnets may be configured to determine a position of beam delivery. This configuring may be more energy efficient using the spiral pattern than a raster pattern or otherwise.

FIG. 15 illustrates a technique 1500, including an operation 1402 for determining a plurality of spots in the target for a gantry angle, wherein the plurality of spots are configured in a spiral pattern. The plurality of spots may be equivalent to the beamlets (e.g., in size). The spots may be contiguously located (e.g., within the target, on a layer). In an example, spots located at an outside edge of the target may have a smaller diameter than spots located at a position inside the target (e.g., not on an outside edge or more centrally located to the target). Beamlets associated with larger diameter spots may have a greater dose than beamlets associated with smaller diameter spots. In an example, intensity modulation of the larger diameter spots is greater than the smaller diameter spots. A spot may include a location (e.g., within a layer of a target). A spot may include a diameter of a beamlet delivered to the location. In an example, a user may select a spot size for the location.

The technique 1400 includes an operation 1404 for ordering the plurality of spots in the spiral pattern from those closest to an isocentric axis for the gantry angle to those most distant from the isocentric axis.

The technique 1400 includes an operation 1406 for continuously delivering a plurality of particle beams as the gantry rotates by delivering a plurality of beamlets for each particle beam of the plurality of particle beams from a beginning of a respective arc to an end of the respective arc according to the spiral pattern of the plurality of spots.

A treatment plan may be developed for the center (e.g., a central angle) of the respective arc, with the respective arc occupying a set of angles (e.g., 5 degrees, 10 degrees, 15 degrees, etc.). A particle beam may include at least one of a plurality of protons, carbon-ions, ions, pions, or positively charged particles. The beamlets may be delivered from a beginning of a respective arc to an end of the respective arc. For example, for a ten degree arc starting at zero degrees, the beamlets may be delivered from zero degrees to ten degrees. In this example, the center of the respective arc may be five degrees.

In an example, the plurality of beamlets may be delivered in a clockwise configuration followed by a counter-clockwise configuration or may be delivered in a counter-clockwise configuration followed by a clockwise configuration. Delivering the plurality of beamlets may include delivering the beamlets from a position inside the target to a position on an outside edge of the target. Delivering the plurality of beamlets may include a single transition between spots of varying size, for example during a spiral pattern. In this example, scanning magnets may be configured to determine a position of beam delivery. This configuring may be more energy efficient using the spiral pattern than a raster pattern or otherwise.

Each of the non-limiting examples described in this document may stand on its own, or may be combined in various permutations or combinations with one or more of the other examples.

Example 1 is a method of delivering a plurality of particle beams from a continuously rotating gantry towards a target, the method comprising: continuously delivering successive particle beams of the plurality of particle beams as the gantry rotates, wherein each particle beam of the successive particle beams has an associated arc, with a center of the associated arc corresponding to a particular gantry angle for each particle beam; for a respective particle beam of the successive particle beams, delivering a plurality of beamlets from a beginning of a respective arc to an end of the respective arc; for a respective gantry angle, determining a plurality of predefined spots in the target for the respective gantry angle, wherein the plurality of predefined spots are configured in a spiral pattern; ordering the plurality of predefined spots in the spiral pattern from those closest to an isocentric axis for the respective gantry angle to those most distant from the isocentric axis; and wherein delivering the successive particle beams includes, delivering the plurality of beamlets for the respective particle beam according to the spiral pattern of the plurality of predefined spots.

In Example 2, the subject matter of Example 1 includes, wherein the plurality of beamlets are delivered in a clockwise configuration followed by a counter-clockwise configuration.

In Example 3, the subject matter of Examples 1-2 includes, wherein a spot of the plurality of predefined spots and a beamlet of the plurality of beamlets are equivalent.

In Example 4, the subject matter of Examples 1-3 includes, wherein the plurality of predefined spots are contiguously located.

In Example 5, the subject matter of Examples 1-4 includes, wherein delivering the plurality of beamlets comprises delivering the plurality of beamlets from a position inside the target to a position on an outside edge of the target.

In Example 6, the subject matter of Examples 1-5 includes, wherein delivering the plurality of beamlets further comprises delivering the plurality of beamlets from a position on an outside edge of the target to a position inside the target.

In Example 7, the subject matter of Examples 1-6 includes, wherein spots of the plurality of predefined spots that are located at an outside edge of the target have a smaller diameter than spots of the plurality of predefined spots located at a position inside the target.

In Example 8, the subject matter of Example 7 includes, wherein beamlets associated with larger diameter spots have a greater dose than the beamlets associated with the smaller diameter spots.

In Example 9, the subject matter of Example 8 includes, wherein intensity modulation of the larger diameter spots is greater than the smaller diameter spots.

In Example 10, the subject matter of Examples 1-9 includes, wherein delivering the plurality of beamlets further comprises a single transition between spots of varying size.

In Example 11, the subject matter of Example 10 includes, wherein configuring scanning magnets to determine a position of beam delivery is more energy efficient using the spiral pattern.

In Example 12, the subject matter of Examples 1-11 includes, wherein a spot of the plurality of predefined spots comprises a location.

In Example 13, the subject matter of Example 12 includes, wherein the spot of the plurality of predefined spots is configured to include a diameter of a beamlet delivered to the location.

In Example 14, the subject matter of Examples 12-13 includes, wherein a user selects a spot size for the location.

In Example 15, the subject matter of Examples 1-14 includes, wherein the particle beam comprises at least one of a plurality of protons, carbon-ions, ions, pions, or positively charged particles.

Example 16 is a non-transitory machine-readable medium including instructions for delivering a plurality of particle beams from a continuously rotating gantry towards a target, which when executed by a processor, cause the processor to: determine a plurality of spots in the target for a gantry angle, wherein the plurality of spots are configured in a spiral pattern; order the plurality of spots in the spiral pattern from those closest to an isocentric axis for the gantry angle to those most distant from the isocentric axis; and continuously deliver the plurality of particle beams as the gantry rotates by delivering a plurality of beamlets for each particle beam of the plurality of particle beams from a beginning of a respective arc to an end of the respective arc according to the spiral pattern of the plurality of spots, wherein a center of the respective arc corresponds to a particular gantry angle for a respective particle beam.

In Example 17, the subject matter of Example 16 includes, wherein the plurality of beamlets are delivered in a clockwise configuration followed by a counter-clockwise configuration.

In Example 18, the subject matter of Examples 16-17 includes, wherein the plurality of spots are contiguously located.

In Example 19, the subject matter of Examples 16-18 includes, wherein spots of the plurality of spots that are located at an outside edge of the target have a smaller diameter than spots of the plurality of predefined spots located at a position inside the target, wherein beamlets associated with larger diameter spots have a greater dose than the beamlets associated with the smaller diameter spots, and wherein intensity modulation of the larger diameter spots is greater than the smaller diameter spots.

In Example 20, the subject matter of Examples 16-19 includes, wherein delivering the plurality of beamlets further comprises a single transition between spots of varying size.

In Example 21, the subject matter of Examples 16-20 includes, wherein the particle beam comprises at least one of a plurality of protons, carbon-ions, ions, pions, or positively charged particles.

Example 22 is a system for delivering a plurality of particle beams from a continuously rotating gantry towards a target, the system comprising: an ion source configured to provide a stream of particles to an injector, the injector configured to accelerate the stream of particles; an accelerator configured to further accelerate the stream of particles and provide energy to the stream of particles, the energy corresponding to a delivery depth within tissue; an energy selector configured to select energies of the stream of particles to be delivered; a plurality of bending magnets configured to transport the stream of particles into a radiation therapy delivery room; a plurality of scanning magnets configured to shape the stream of particles according to a target; a snout configured to: continuously deliver successive particle beams of the stream of particles as the gantry rotates, wherein each particle beam of the successive particle beams has an associated arc, with a center of the associated arc corresponding to a particular gantry angle for each particle beam; for a respective particle beam of the successive particle beams, deliver a plurality of beamlets from a beginning of a respective arc to an end of the respective arc; and a processor configured to: for a respective gantry angle, determine a plurality of predefined spots in the target for the respective gantry angle, wherein the plurality of predefined spots are configured in a spiral pattern; order the plurality of predefined spots in the spiral pattern from those closest to an isocentric axis for the respective gantry angle to those most distant from the isocentric axis; and wherein delivery of the successive particle beams includes, delivery of the plurality of beamlets for the respective particle beam according to the spiral pattern of the plurality of predefined spots.

In Example 23, the subject matter of Example 22 includes, wherein the particle beam comprises at least one of a plurality of protons, carbon-ions, ions, pions, or positively charged particles.

In Example 24, the subject matter of Examples 22-23 includes, wherein the plurality of beamlets are delivered in a clockwise configuration followed by a counter-clockwise configuration.

In Example 25, the subject matter of Examples 22-24 includes, wherein a spot of the plurality of predefined spots and a beamlet of the plurality of beamlets are equivalent.

In Example 26, the subject matter of Examples 22-25 includes, wherein the plurality of predefined spots are contiguously located.

In Example 27, the subject matter of Examples 22-26 includes, wherein to deliver the plurality of beamlets, the snout is further configured to deliver the plurality of beamlets from a position inside the target to a position on an outside edge of the target.

In Example 28, the subject matter of Examples 22-27 includes, wherein to deliver the plurality of beamlets, the snout is further configured to deliver the plurality of beamlets from a position on an outside edge of the target to a position inside the target.

In Example 29, the subject matter of Examples 22-28 includes, wherein spots of the plurality of predefined spots that are located at an outside edge of the target have a smaller diameter than spots of the plurality of predefined spots located at a position inside the target.

In Example 30, the subject matter of Example 29 includes, wherein beamlets associated with larger diameter spots have a greater dose than the beamlets associated with the smaller diameter spots.

In Example 31, the subject matter of Example 30 includes, wherein intensity modulation of the larger diameter spots is greater than the smaller diameter spots.

In Example 32, the subject matter of Examples 22-31 includes, wherein to deliver the plurality of beamlets, the snout is further configured to deliver the plurality of beamlets with a single transition between spots of varying size.

In Example 33, the subject matter of Example 32 includes, wherein configuring scanning magnets to determine a position of beam delivery is more energy efficient using the spiral pattern.

In Example 34, the subject matter of Examples 22-33 includes, wherein a spot of the plurality of predefined spots comprises a location.

In Example 35, the subject matter of Example 34 includes, wherein the spot of the plurality of predefined spots is configured to include a diameter of a beamlet delivered to the location.

In Example 36, the subject matter of Examples 34-35 includes, wherein a user selects a spot size for the location.

Example 37 is at least one machine-readable medium including instructions that, when executed by processing circuitry, cause the processing circuitry to perform operations to implement of any of Examples 1-36.

Example 38 is an apparatus comprising means to implement of any of Examples 1-36.

Example 39 is a system to implement of any of Examples 1-36.

Example 40 is a method to implement of any of Examples 1-36.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the invention should be determined with reference to the appended claims, along with the full scope of equivalents to which such claims are entitled.

The claimed invention is:

1. A method of delivering a plurality of particle beams from a continuously rotating gantry towards a target, the method comprising:

continuously delivering successive particle beams of the plurality of particle beams as the gantry rotates, wherein each particle beam of the successive particle beams has an associated arc, with a center of the associated arc corresponding to a particular gantry angle for each particle beam;

for a respective particle beam of the successive particle beams, delivering a plurality of beamlets from a beginning of a respective arc to an end of the respective arc;

for a respective gantry angle, determining a plurality of predefined spots in the target for the respective gantry angle, wherein the plurality of predefined spots are configured in a spiral pattern;

ordering the plurality of predefined spots in the spiral pattern from those closest to an isocentric axis for the respective gantry angle to those most distant from the isocentric axis; and wherein delivering the successive particle beams includes delivering the plurality of beamlets for the respective particle beam according to the spiral pattern of the plurality of predefined spots.

2. The method of claim 1, wherein the plurality of beamlets are delivered in a clockwise configuration followed by a counter-clockwise configuration.

3. The method of claim 1, wherein a spot of the plurality of predefined spots and a beamlet of the plurality of beamlets are equivalent.

4. The method of claim 1, wherein the plurality of predefined spots are contiguously located.

5. The method of claim 1, wherein delivering the plurality of beamlets comprises delivering the plurality of beamlets from a position inside the target to a position on an outside edge of the target.

6. The method of claim 1, wherein delivering the plurality of beamlets further comprises delivering the plurality of beamlets from a position on an outside edge of the target to a position inside the target.

7. The method of claim 1, wherein spots of the plurality of predefined spots that are located at an outside edge of the target have a smaller diameter than spots of the plurality of predefined spots located at a position inside the target.

8. The method of claim 7, wherein beamlets associated with larger diameter spots have a greater dose than the beamlets associated with the smaller diameter spots.

9. The method of claim 8, wherein intensity modulation of the larger diameter spots is greater than the smaller diameter spots.

10. The method of claim 1, wherein delivering the plurality of beamlets further comprises a single transition between spots of varying size.

11. The method of claim 1, wherein a spot of the plurality of predefined spots comprises a location.

12. The method of claim 11, wherein the spot of the plurality of predefined spots is configured to include a diameter of a beamlet delivered to the location.

13. The method of claim 11, wherein a user selects a spot size for the location.

14. The method of claim 1, wherein the particle beam comprises at least one of a plurality of protons, carbon-ions, ions, pions, or positively charged particles.

15. A non-transitory machine-readable medium including instructions for delivering a plurality of particle beams from a continuously rotating gantry towards a target, which when executed by a processor, cause the processor to:
determine a plurality of spots in the target for a gantry angle, wherein the plurality of spots are configured in a spiral pattern;
order the plurality of spots in the spiral pattern from those closest to an isocentric axis for the gantry angle to those most distant from the isocentric axis; and
continuously deliver the plurality of particle beams as the gantry rotates by delivering a plurality of beamlets for each particle beam of the plurality of particle beams from a beginning of a respective arc to an end of the respective arc according to the spiral pattern of the plurality of spots, wherein a center of the respective arc corresponds to a particular gantry angle for a respective particle beam.

16. The machine-readable medium of claim 15, wherein the plurality of beamlets are delivered in a clockwise configuration followed by a counter-clockwise configuration.

17. The machine-readable medium of claim 15, wherein the plurality of spots are contiguously located.

18. The machine-readable medium of claim 15, wherein spots of the plurality of spots that are located at an outside edge of the target have a smaller diameter than spots of the plurality of predefined spots located at a position inside the target, wherein beamlets associated with larger diameter spots have a greater dose than the beamlets associated with the smaller diameter spots, and wherein intensity modulation of the larger diameter spots is greater than the smaller diameter spots.

19. The machine-readable medium of claim 15, wherein delivering the plurality of beamlets further comprises a single transition between spots of varying size.

20. The machine-readable medium of claim 15, wherein the particle beam comprises at least one of a plurality of protons, carbon-ions, ions, pions, or positively charged particles.

21. A system for delivering a plurality of particle beams from a continuously rotating gantry towards a target, the system comprising:
an ion source configured to provide a stream of particles to an injector, the injector configured to accelerate the stream of particles;
an accelerator configured to further accelerate the stream of particles and provide energy to the stream of particles, the energy corresponding to a delivery depth within tissue;
an energy selector configured to select energies of the stream of particles to be delivered;
a plurality of bending magnets configured to transport the stream of particles into a radiation therapy delivery room;
a plurality of scanning magnets configured to shape the stream of particles according to a target;
a snout configured to:
continuously deliver successive particle beams of the stream of particles as the gantry rotates, wherein each particle beam of the successive particle beams has an associated arc, with a center of the associated arc corresponding to a particular gantry angle for each particle beam;
for a respective particle beam of the successive particle beams, deliver a plurality of beamlets from a beginning of a respective arc to an end of the respective arc; and
a processor configured to:
for a respective gantry angle, determine a plurality of predefined spots in the target for the respective gantry angle, wherein the plurality of predefined spots are configured in a spiral pattern;
order the plurality of predefined spots in the spiral pattern from those closest to an isocentric axis for the respective gantry angle to those most distant from the isocentric axis; and
wherein delivery of the successive particle beams includes delivery of the plurality of beamlets for the respective particle beam according to the spiral pattern of the plurality of predefined spots.

22. The system of claim 21, wherein the particle beam comprises at least one of a plurality of protons, carbon-ions, ions, pions, or positively charged particles.

23. The system of claim 21, wherein the plurality of beamlets are delivered in a clockwise configuration followed by a counter-clockwise configuration.

24. The system of claim 21, wherein a spot of the plurality of predefined spots and a beamlet of the plurality of beamlets are equivalent.

25. The system of claim 21, wherein the plurality of predefined spots are contiguously located.

26. The system of claim 21, wherein to deliver the plurality of beamlets, the snout is further configured to deliver the plurality of beamlets from a position inside the target to a position on an outside edge of the target.

27. The system of claim 21, wherein to deliver the plurality of beamlets, the snout is further configured to deliver the plurality of beamlets from a position on an outside edge of the target to a position inside the target.

28. The system of claim 21, wherein spots of the plurality of predefined spots that are located at an outside edge of the target have a smaller diameter than spots of the plurality of predefined spots located at a position inside the target.

29. The system of claim 28, wherein beamlets associated with larger diameter spots have a greater dose than the beamlets associated with the smaller diameter spots.

30. The system of claim 29, wherein intensity modulation of the larger diameter spots is greater than the smaller diameter spots.

31. The system of claim 21, wherein to deliver the plurality of beamlets, the snout is further configured to deliver the plurality of beamlets with a single transition between spots of varying size.

32. The system of claim 21, wherein a spot of the plurality of predefined spots comprises a location.

33. The system of claim 32, wherein the spot of the plurality of predefined spots is configured to include a diameter of a beamlet delivered to the location.

34. The system of claim 32, wherein the processor is further configured to receive a user selection of a spot size for the location.

* * * * *